US009265647B2

(12) United States Patent
Desousa

(10) Patent No.: US 9,265,647 B2
(45) Date of Patent: Feb. 23, 2016

(54) DYNAMIC LOAD BEARING SHOCK ABSORBING EXOSKELETAL KNEE BRACE

(71) Applicant: Egas Jose-Joaquim Desousa, Grand Blanc, MI (US)

(72) Inventor: Egas Jose-Joaquim Desousa, Grand Blanc, MI (US)

(*) Notice: Subject to any disclaimer, the term of this patent is extended or adjusted under 35 U.S.C. 154(b) by 0 days.

(21) Appl. No.: 14/465,556

(22) Filed: Aug. 21, 2014

(65) Prior Publication Data

US 2014/0364783 A1    Dec. 11, 2014

Related U.S. Application Data

(63) Continuation of application No. 14/104,381, filed on Dec. 12, 2013, now abandoned, which is a continuation-in-part of application No. 13/902,835, filed on May 26, 2013, now abandoned, which is a continuation-in-part of application No. 13/555,165, filed on Aug. 9, 2012, now abandoned.

(51) Int. Cl.
*A61F 5/00* (2006.01)
*A61F 5/01* (2006.01)

(52) U.S. Cl.
CPC .............. *A61F 5/0125* (2013.01); *A61F 5/0102* (2013.01); *A61F 5/0123* (2013.01); *A61F 2005/0169* (2013.01)

(58) Field of Classification Search
CPC .............. A61F 5/0102; A61F 5/0123; A61F 2005/0169; A61F 2005/0179; A61F 5/0106; A61F 2005/0144; A61F 2005/0146; A61F 2/36; A61F 5/0125; A61F 2005/0139; A61F 2005/0148; A61F 2005/0167; A61F 5/0104; A61F 2002/607; A61F 2005/0158; A61F 2/66; A61F 2/72; A61F 5/0585; A61B 5/0031; A61B 5/03; A63B 21/0085; A63B 23/04; A63B 69/0064; A63B 69/18; A63B 21/00072; A63B 21/00065; A63C 11/00
USPC ........................... 602/23–28; 128/882; 5/624
See application file for complete search history.

(56) References Cited

U.S. PATENT DOCUMENTS

| | | |
|---|---|---|
| 2,267,848 A | 12/1941 | Taylor |
| 2,516,253 A | 7/1950 | Pieterick |
| 4,450,832 A | 5/1984 | Waddell |
| 4,522,199 A | 6/1985 | Waddell et al. |
| 4,688,599 A | 8/1987 | Zeman |
| RE32,650 E | 4/1988 | Waddell |
| 4,961,416 A * | 10/1990 | Moore et al. ............ 602/26 |
| 5,352,190 A | 10/1994 | Fischer et al. |
| 5,645,524 A | 7/1997 | Doyle |
| 6,024,713 A | 2/2000 | Barney |
| 7,578,799 B2 * | 8/2009 | Thorsteinsson et al. ....... 602/5 |
| 8,114,034 B2 | 2/2012 | Ikeuchi et al. |
| 2003/0109817 A1 | 6/2003 | Berl |
| 2011/0071452 A1 * | 3/2011 | Auberger ............ 602/26 |
| 2013/0245524 A1 * | 9/2013 | Schofield ............ 602/16 |

* cited by examiner

*Primary Examiner* — Michael Brown
(74) *Attorney, Agent, or Firm* — Dinsmore & Shohl LLP

(57) ABSTRACT

The exoskeletal dynamic load bearing shock absorbing knee brace makes use of the energy absorbing characteristics of specifically designed industrial shock absorbers which are held precisely in place by an articulated dynamic exoskeletal structure that is to be secured to the lower limbs of the individual with the injured knee. The exoskeletal structure is designed using the principles of the overcenter linkage to translate and transfer to the shock absorbers a representative fraction of the normal and extra normal ambulatory movements of the lower limbs of the user which makes possible for these shock absorbers to absorb a corresponding amount of energy and provide an alternate load bearing structure parallel to the knees thus introducing a desirable degree of protection for the injured knee.

35 Claims, 34 Drawing Sheets

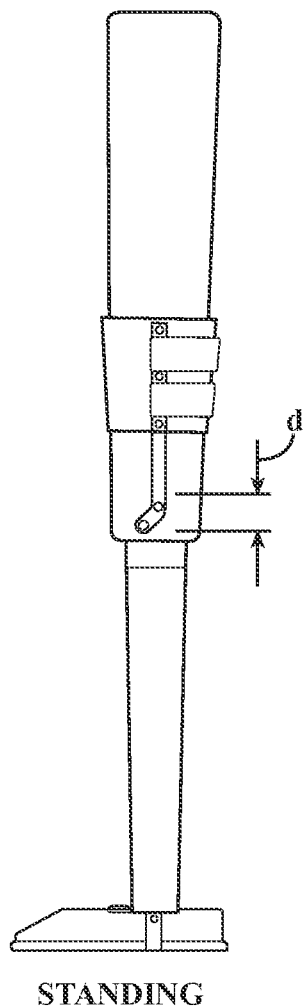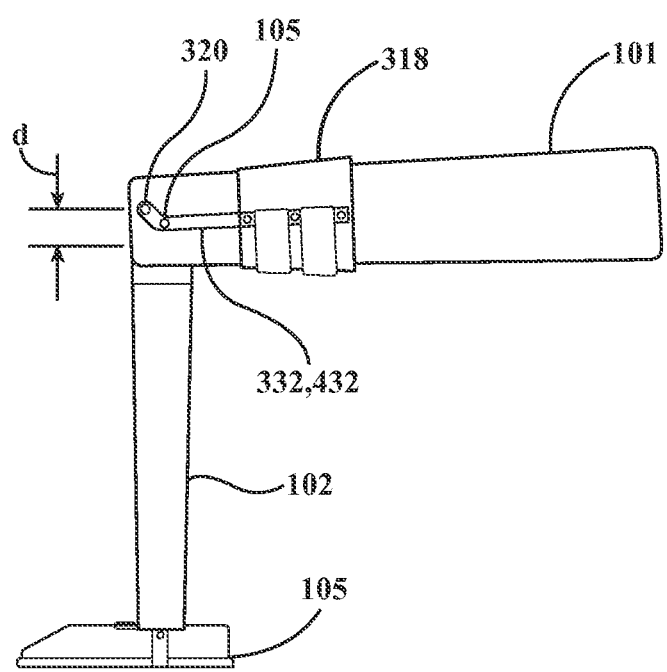
FIG. 22  STANDING
FIG. 23  SITTING

DYNAMIC LOAD BEARING SHOCK ABSORBING EXOSKELETAL KNEE BRACE

CROSS-REFERENCE TO RELATED APPLICATIONS

This is a continuation of U.S. Ser. No. 14/104,381, filed Dec. 12, 2013, which is a continuation-in-part of U.S. Ser. No. 13/902,835, filed May 26, 2013, which is a continuation-in-part of U.S. Ser. No. 13/555,165, filed Aug. 9, 2012.

TECHNICAL FIELD

A knee brace incorporating external shock absorbers configured to provide shock absorption of an articulated leg so as to reduce shock to the knee is provided.

BACKGROUND OF THE INVENTION

Injuries to the human knee joint resulting from participation in extreme sporting activities or resulting from accumulated damage with advancing years are all too common.

The knee joint is the biggest joint in the human body and is subject to various failure modes. One of the failure modes is the failure of the meniscus to maintain its integrity under sudden load spikes or accumulated damage. The meniscus is an avascular cartilage that acts as a shock absorber inside the knee. There are two disc shaped menisci in each knee. FIG. 1 is a representation of the knee with the meniscus between the femur and the tibia.

A Sep. 11, 2008 study in the New England Journal of Medicine titled Incidental Meniscal Findings on Knee MRI in Middle-Aged and Elderly Persons by seven physicians in the New England area concluded that "Incidental Meniscal findings on MRI of the knee are common in the general population and increase with increasing age." The study reports Meniscal tear prevalence rates of 15% to 30% in women and men aged 50-59 and 27% to 37% rates in women and men aged 60-69. The incidence rates increase to a maximum of 50% with age advancing to 70-90 years.

The damage resulting from meniscus tears and other failure modes is hard to contain and control under normal everyday working load situations. As the meniscus failure progresses the femur and the tibia come in direct contact resulting in irreversible damage under very painful conditions. If untreated, the afflicted may find it unable to bear the pain, and may require the implantation of artificial knees.

Knee braces and supporting orthotics currently available are not configured to provide load bearing, and shock absorbing function. For instance, U.S. Pat. No. 4,688,599 to Vito et al. is designed to provide stability in cases of loss of neuromuscular control of a knee joint or a hip joint. U.S. Pat. No. 5,645,524 to Doyle is directed towards a knee support for supporting an injured knee while permitting bending and straightening of such a knee, however is silent as to shock absorbing functionality. U.S. Pat. No. 5,352,190 to Fischer et al. is directed towards a device for bracing or exercising the knee joint in a manner that allows the bending of the knee joint only along a predetermined path which approximates the bending of the joint.

Accordingly it remains desirable to have a knee brace that bears the load of the knees and absorbs shock on the knees so as to prevent damage to the knees and help in the healing of the damaged knee joint. It further remains desirable to have a knee brace worn around the knee and allow the individual to maintain flexibility and movement of the knee so as to allow individuals with knee problems to continue with their active lifestyle.

SUMMARY OF THE PRESENT INVENTION

A load bearing shock absorbing knee brace is provided. The knee brace is configured to be attached to the lower portion of the leg surrounding the tibia and an upper portion of the leg around the femur so as to reduce the load and the shock loads experienced by the knee joint as the individual uses the legs to walk or run.

In a first embodiment, the knee brace an upper sleeve assembly having a pair of upper struts fixed. One end of the upper struts are fixed to the sleeve. The sleeve is configured to engage the outer surface of the upper limb or thigh. The sleeve may have a conical shape similar to that of the human thigh to facilitate the desired load transfer from the sleeve to the thigh without the use of uncomfortably tight fits.

The other end of the struts are pivotally attached to a pair of shock absorbers. The shock absorbers may be tuned to specific energy absorption capabilities taking into account the effective impact weight of the individual using the knee brace, shock absorber stroke, internal return spring force and ease of integration. The shock absorbers are retained in a load bearing yet adjustable manner in a lower strut section that is to be strapped to the lower limbs. The other end of the lower strut may be removably attached to a shoe insert. The end of the lower strut may be inserted via a quick disconnect mechanism into a suitably designed hinged mechanism that is made part of a specially designed and built shoe.

The overcenter linkage principle that is being used to actuate the shock absorbers utilizing the natural movement of the limbs can be best be explained by reference to the diagrams in FIGS. 2 and 3. In these figures 701 and 704 represent two points at which this knee brace is strapped to the limb: (1) the point in the thigh where the strap is attached; and (2) the point in the shoe where the lower strut is attached. The center point of the clevis pin in the shock absorber is represented by 702 while 703 represents the natural center of the knee. With the individual in the seated position the length of the linkage 701-702-704 is greater that the length of the path in the leg 701-703-704.

Thus, when the individual stands up in the vertical position for instance, the movement of the leg forces the linkage 701-702-704 to decrease in length thereby forcing the shock absorber to close in until the new linkage length equals the length of the path in the leg 701-703-704. In this position the shock absorber is primed for action and the return springs push up against upper sleeve as far as the fastening conditions permit. As the individual walks or runs the movement of the limbs introduces sufficient movement to the shock absorbers to elicit a force response which helps in reducing the load on the knee. The shock absorber may be dimensioned to provide a force response directly proportional to the rate of change of position of its piston thus more vigorous and faster movements elicit a greater force response, and this helps reduce the load on the knee under shock and faster movement conditions.

The knee brace is configured to provide load bearing and shock absorbing function to the user's knee. It should be appreciated that the lower struts and the incorporation of the shoe insert to the shoe may be modified. In the first preferred embodiment the lower strut is pivotably connected to the back of the heel. This design allows the greatest degree of freedom for the foot. In a second preferred embodiment, the lower strut is pivotably mounted to a shoe sole insert having a pair of upwardly extending arms. For instance, the lower strut assembly may include a pair of lower struts, each fixedly connected to the pair of shock absorbers on one end, and pivotably connected to the pair of upwardly extending arms on the other end. In a third preferred embodiment, the knee brace may have a lower strut which includes a retaining sleeve configured to hold the pair of shock absorbers on one end of the lower strut, and a pair of retainers disposed on the end opposite the retaining sleeve, wherein the ends of the retainers are pivotably connected to a respective boot configured to engage a respective upwardly extending arm so as to position the lower strut in front of the calf when worn. In a fourth preferred embodiment, the knee brace includes a Y-shaped member configured to provide space for the knee to flex. In a fifth preferred embodiment, the knee brace includes a shock absorber support assembly configured to house the shock absorber coaxially with the lower strut.

In operation, the individual puts on the specially designed shoe with the load bearing insert in the seated position. In this position the individual inserts the lower strut assembly boots onto the shoe support hinged pin. He can at this point strap the lower linkage to his calf with the strap provided by fastening snugly the straps fitted a fastener such as a buckle or Velcro.

At this point he rolls the cuff detail snugly over his tight and fastens it tight with the two straps provided using the buckle or the Velcro fasteners. The axis of the clevis pin of the shock absorber should be a certain distance away from the natural axis of the knee based on the design of the exoskeletal brace.

As the individual stands up he can feel the upper cuff snug up tight as the shock absorber is actuated and the return spring pushes the clevis end up.

By walking back and forth the individual can feel the shock absorber absorb part of the load on the knee. This results in immediate relief from the pain as the femur and tibia contact is reduced.

BRIEF DESCRIPTION OF THE DRAWINGS

With reference to the attached drawings in which like reference numbers refer to like parts:

FIGS. 22 and 23 show a representation of the magnified pivot point movement achieved with the upper struts used in the fourth and fifth preferred embodiment of the brace.

DETAILED DESCRIPTION OF THE INVENTION

Figure 1:
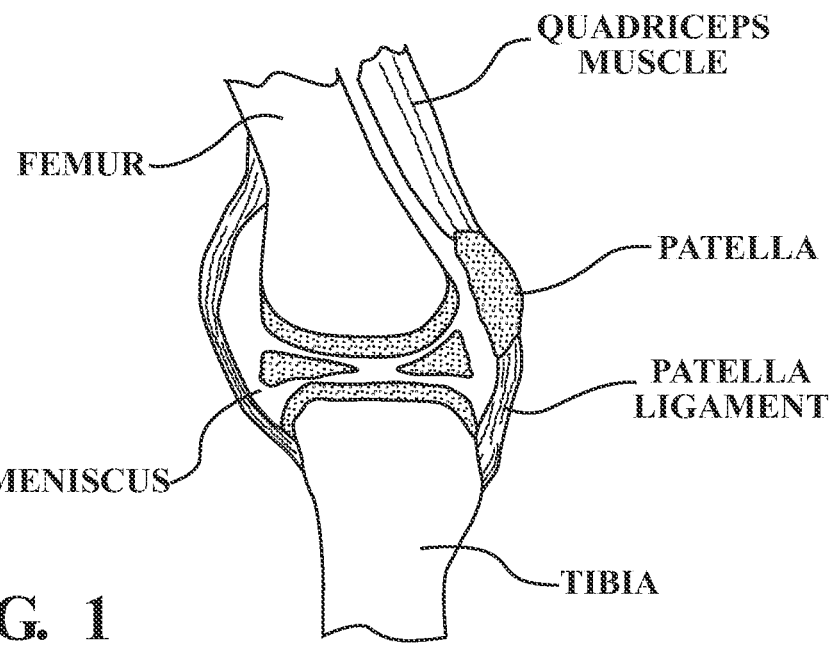
FIG. 1 shows a representation of the human knee joint with the meniscus in between the femur and the tibia.

FIG. 1 shows a diagram of the lateral view of the human knee. The meniscus cartilage is represented in the cross sectional view as triangular bodies that help keep the femur and tibia in place and act as internal shock absorbers. The failure mode of the meniscus generally manifests in tears to the meniscus body which gradually deteriorates and the resulting contact between the femur and the tibia leads to sequence of events that cause a lot of pain and tend to force the afflicted individual to refrain from many of their normal ambulatory activities.

Figures 2, 3:
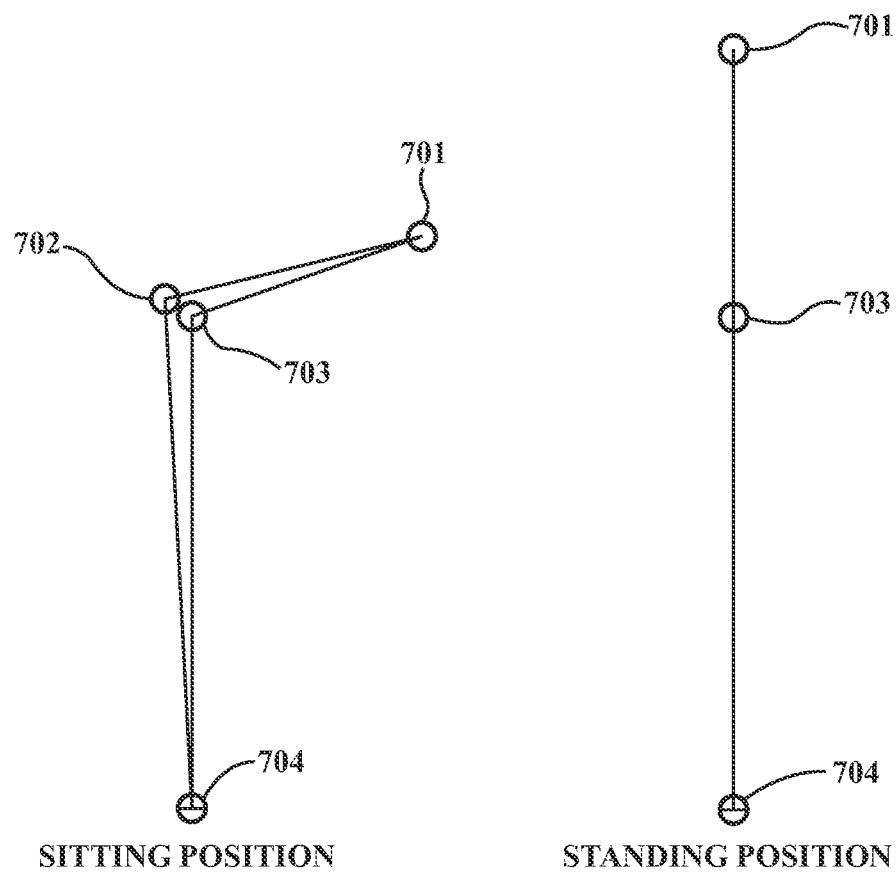
FIG. 2 and FIG. 3 show a representation of the "overcenter" linkage principle that is being used in this invention.

FIGS. 2 and 3 show a diagram used to describe the overcenter linkage principle that is being used in the knee brace described herein. The overcenter linkage principle, utilizing the natural movement off the limbs, is being used to actuate the shock absorbers of the knee brace. The movement of the knee brace is illustrated by reference to the diagrams in FIGS. 2 and 3. In these diagrams, 701 and 704 represent two points at which the knee brace is strapped to the limb: (1) the point in the thigh where the strap is attached; and (2) the point in the shoe where the lower strut is attached. The first pivot point of the brace is represented by 702 while 703 represents the natural center of the knee. With the individual in the seated position the length of the linkage 701-702-704 is greater that the length of the path in the leg 701-703-704.

Thus, when the individual stands up in the vertical position for instance, the movement of the leg forces the linkage 701-702-704 to decrease in length thereby forcing the shock absorber to close in until the new linkage length equals the length of the path in the leg 701-703-704. In this position the shock absorber is primed for action and the return springs push up against upper sleeve as far as the fastening conditions permit. As the individual walks or runs the movement of the limbs introduces sufficient movement to the shock absorbers to elicit a force response which helps in reducing the load on the knee. The shock absorber may be configured to provide a force response directly proportional to the rate of change of position of its piston thus more vigorous and faster movements elicit a greater force response, and this helps reduce the load on the knee under shock conditions and faster movement conditions.

Figure 4:
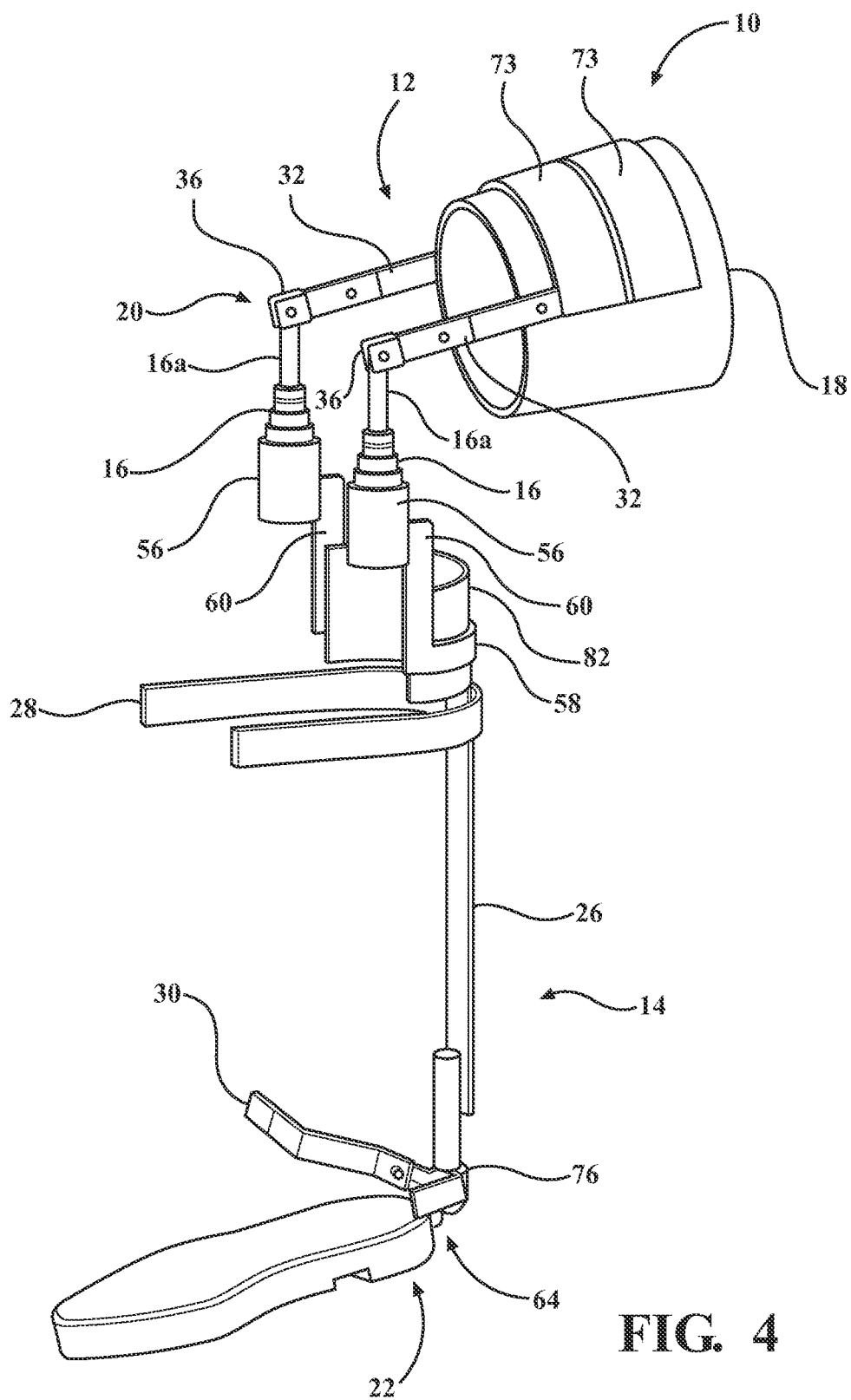
FIG. 4 is an isometric view of the first preferred embodiment of the knee brace with the strut support at the back of the leg.

FIG. 4 shows an isometric view of a first preferred embodiment of the exoskeletal load bearing, shock absorbing knee brace 10 with the individual in the seated position. The brace 10 includes an upper sleeve assembly 12, a lower strut assembly 14 and a pair of shock absorbers 16. The upper sleeve assembly 12 includes a sleeve 18 configured to engage the outer surface of the thigh portion of a leg. The lower strut assembly 14 is configured to engage the calf. The shock absorbers 16 are pivotably mounted to one of either the upper sleeve assembly 12 or the lower strut assembly 14 about a first pivot point 20. The first pivot point 20 is positioned above the pivot point of the knee, indicated by 703 in FIGS. 2 and 3, so as to actuate the pair of shock absorbers 16 to the decompressed position when the leg is articulated, thereby absorbing the shock imparted on the knee.

The knee brace 10 may further include a load bearing shoe sole insert 22. The shoe sole insert 22 is configured to be positioned within the shoe 24 of a user. The shoe sole insert 22 may be pivotably mounted to the lower strut assembly 14. In a first preferred embodiment of the brace 10, the shoe sole insert 22 is shown pivotably attached to a lower strut 26 at the back of the heel portion of the shoe sole insert 22. However, it should be appreciated that the sole insert 22 may be pivotably attached to the lower strut assembly 14 about a point other than the back heel as described further below.

Figure 5:
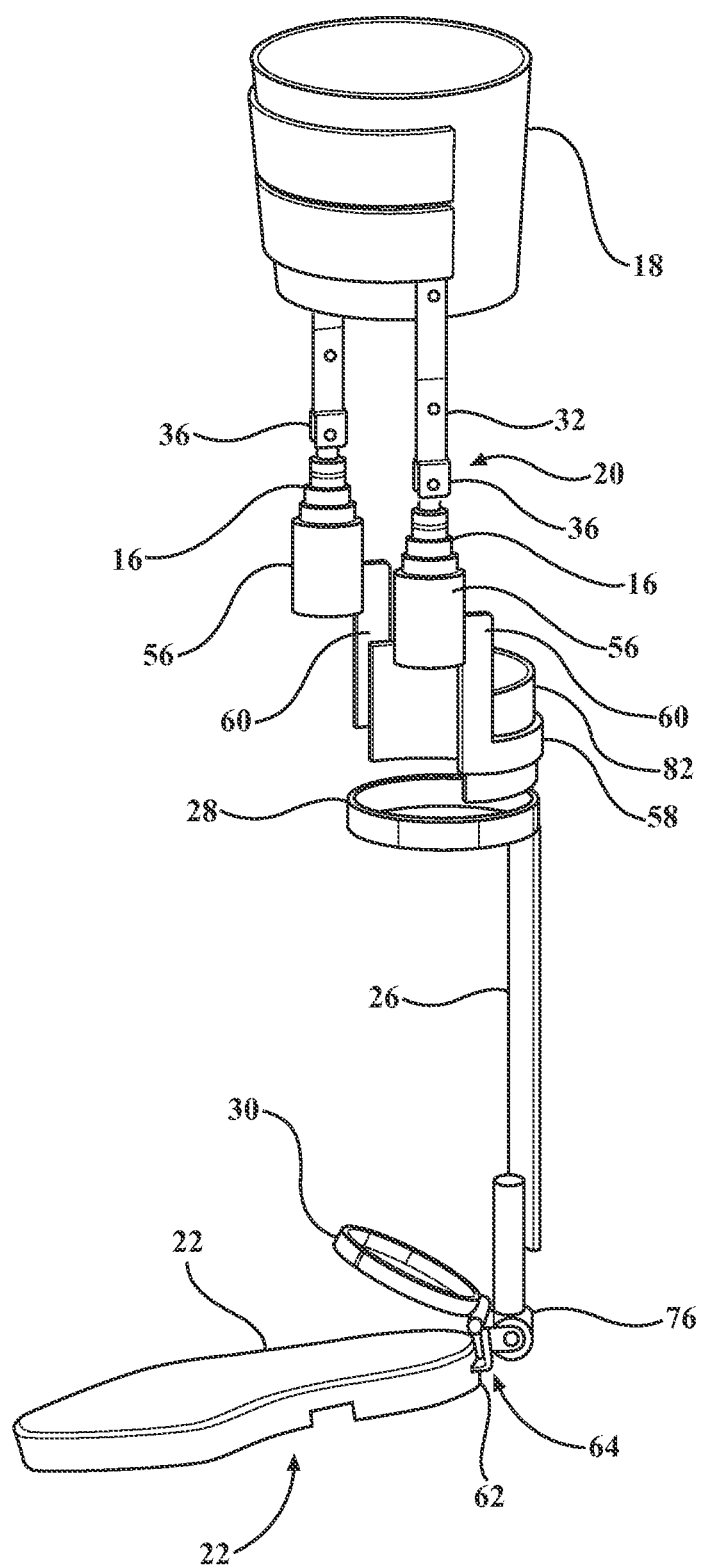
FIG. 5 is a perspective view of the knee brace of FIG. 4 in a straightened/standing position.

The person who is to wear the brace 10 is not shown in the drawing but the position of the shoe sole insert 22 helps infer the actual position of the leg as it would be with the thigh wrapped with the sleeve 18, and the calf is secured with a first lower attachment 28, and the ankle, a second lower attachment 30. FIG. 5 shows an isometric view of the knee brace 10 in FIG. 4 but with the individual in standing position with the wherein the first and lower attachments 28, 30 are straps that are wrapped around the calf and the ankle and the shock absorber in the compressed position as depicted by the shock absorber rod positions 322.

Figure 12:
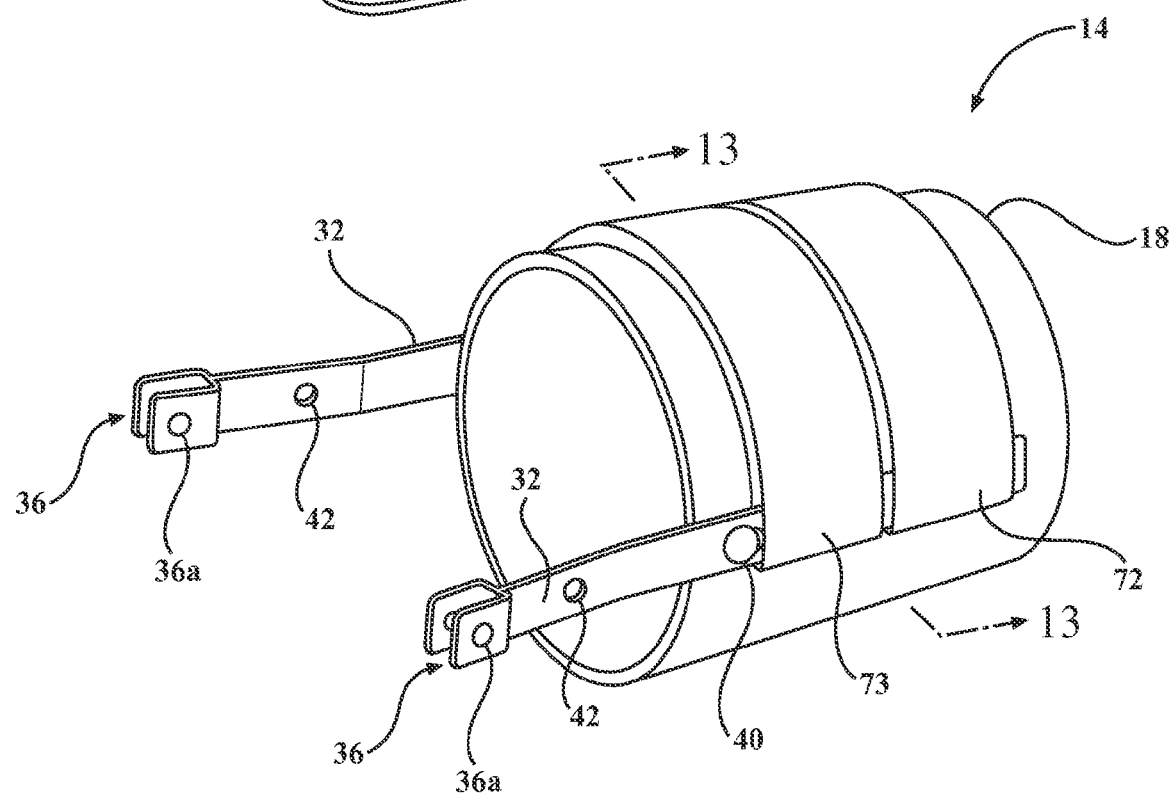
FIG. 12 is an isometric view of the upper sleeve assembly.
Figure 13:
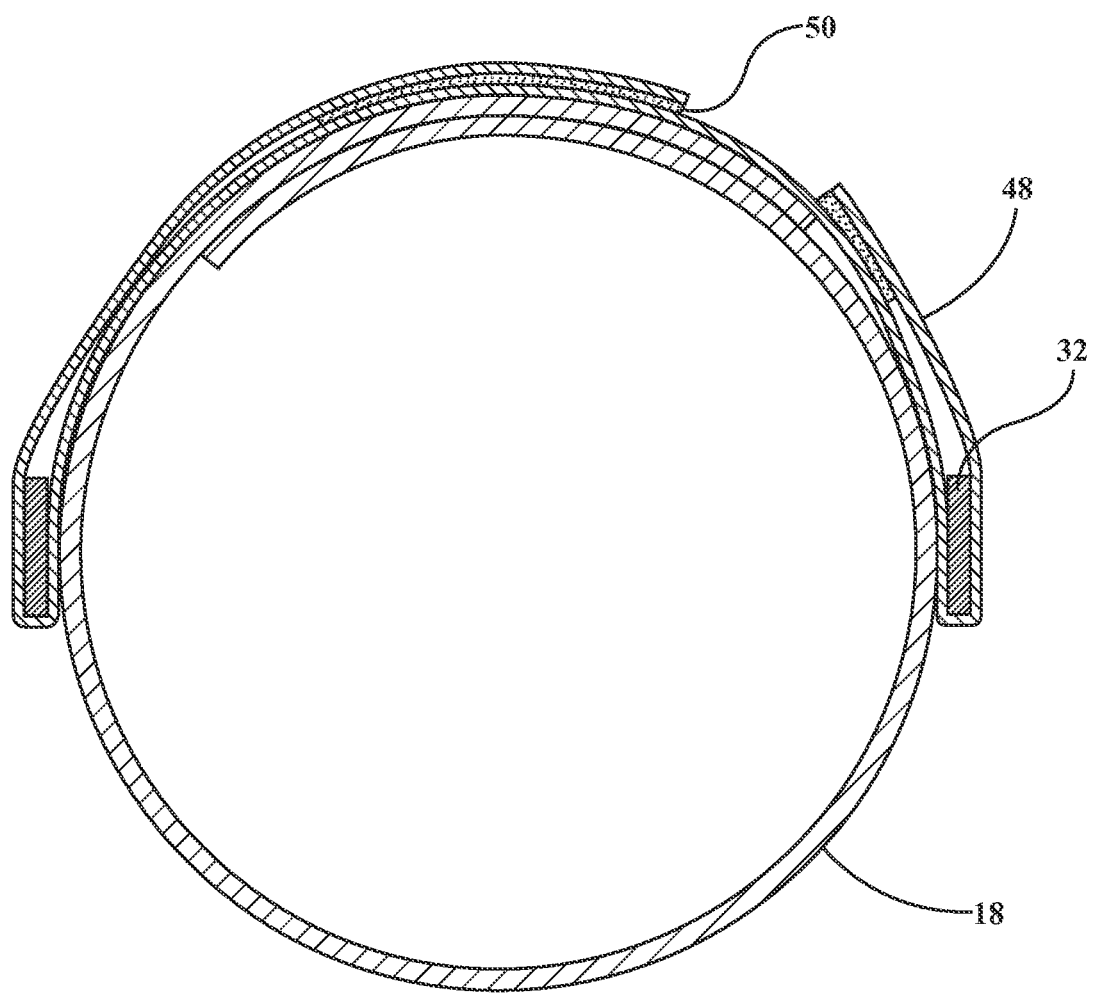
FIG. 13 is a cross sectional view of the upper sleeve assembly taken along line 13-13.
Figure 15:
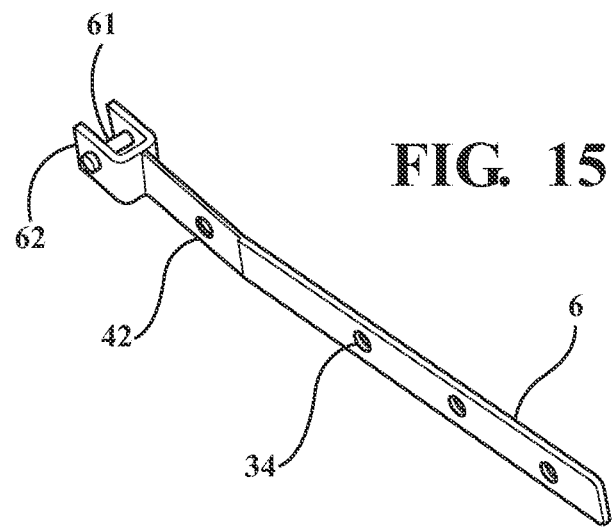
FIG. 15 is an isometric view of the upper strut.

With reference now to FIGS. 12, 13, and 15 an illustrative view of the upper sleeve assembly 12 is provided. The upper sleeve assembly 12 is also shown as an isometric view in FIG. 12, and in a cross sectional view in FIG. 13 demonstrating the design using a Velcro brand hook and loop fastener 75. With reference first to FIG. 13, the sleeve 18 is a planar sheet of material with one end shown overlapping the other end so as to form to the thigh of a user.

With reference now to FIGS. 12 and 15, the upper sleeve assembly 12 includes a pair of upper struts 32 spaced apart from each other. The upper struts 32 are a generally elongated member include a plurality of holes 34, a lower end of the struts include a lower attachment 36 having a through-hole 36a for which a pin 38 may be mounted so as to pivotably attach the upper struts 32 to a respective shock absorber 16 as shown in FIGS. 4-7. The sleeve 18 is fixedly mounted to a respective upper strut 32. With reference specifically to FIG. 12, a fastener 40, such as a tab, may be used to attach the sleeve 18 to a respective upper strut 32 by inserting the tab through upper strut hole 34 (shown in FIG. 15) and engaging the sleeve 18. The sleeve 18 is made out of a flat material that is strong, flexible and light. One end of the sleeve 18 overlaps the other and the sleeve 18 may be secured to the thigh by the use of a fastening device 73, shown as a pair of straps.

Figure 14:
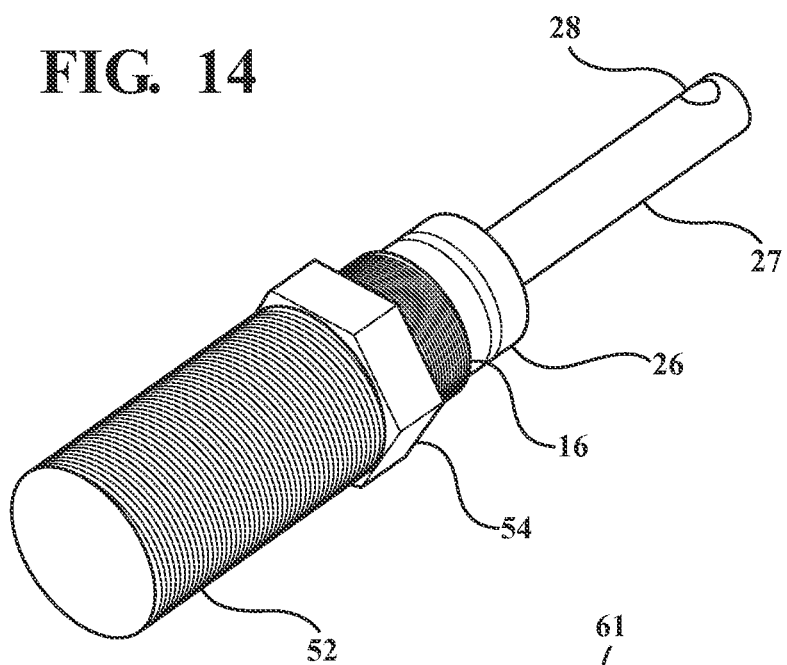
FIG. 14 is an isometric view of the shock absorber.
Figure 20:
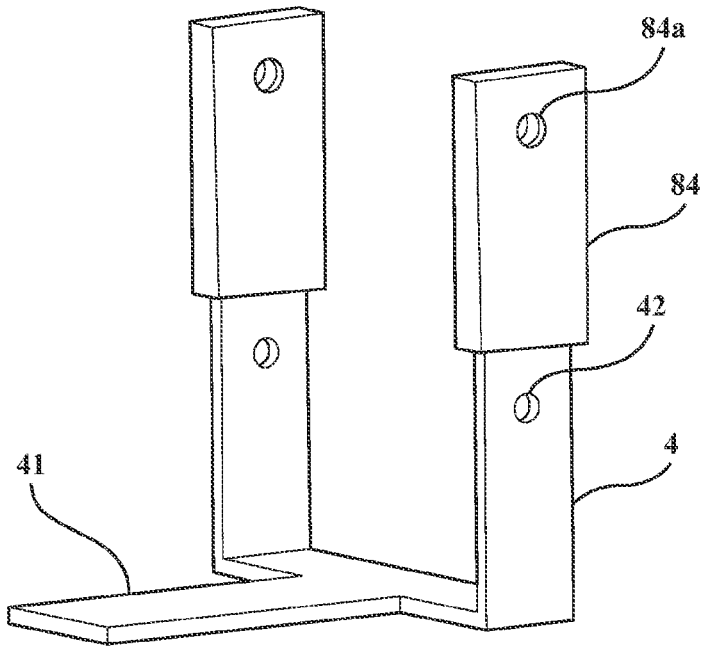
FIG. 20 shows an isometric view of the shoe insert of the second and third preferred embodiment of the knee brace.

The upper struts 32 are fastened to the sleeve 18 is such a manner that when the sleeve 18 is wrapped around the thigh of the individual the upper struts 32 present the lower attachment 36 (shown in FIGS. 12 and 15), shown as clevis ends for insertion of the pins 38 to enable a pivotal connection to the rod end 28 of the shock absorbers 16, also shown in isolation in FIG. 14. The upper strut 32 in FIG. 15 also is provided with comfort pad holes 42 for the attachment of optional comfort pads 44 shown in isolation in FIG. 20, by use of the pad fastener 46 (shown in FIG. 21). With reference also to FIG. 13, a cross sectional view of the sleeve assembly 12 is provided. FIG. 20 shows an upper fastening device 48, shown as straps 48, wrapped around the upper struts 32 which are fastened to the sleeve 18 using fastener 40. Once the sleeve 18 is fitted around the thigh, the sleeve 18 can be held snugly in place by use of a fastener 50, shown as Velcro fasteners.

Figure 21:
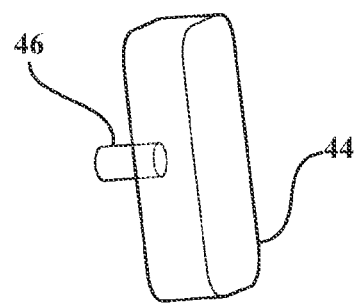
FIG. 21 shows an isometric view of the optional comfort pad that is to be used along with the upper struts.

The sleeve 18 is to be made of a strong yet flexible material such a 4 ply food conveyor belting material lined suitably with a soft yet somewhat sticky layer for comfort of the user. The sleeve 18 is to be wrapped around the thigh or upper limb in a shape that is conical as shown in FIGS. 4, 5, 6 and 8. The sleeve 18 includes an upper opening opposite a lower opening, wherein the upper opening is larger in diameter than the lower opening so as to fit the shape of the average human thigh. In FIG. 21, 44 represents the soft yet durable part of the comfort pad that is to be adjusted to push comfortably against the upper leg of the individual.

FIG. 4 also shows the shock absorber 16 provided externally with a vertical position mounting adjustment mechanism in the form of a threaded body 52 and a nut 54 as shown in the isolated view in FIG. 14. It should be appreciated that the rotation of the nut 54 about the threaded body 52 displaces the shock absorber 16 axially with respect to the lower strut assembly as shown in FIG. 4. The shock absorber 16 may include a drive shaft 16a. The top end of the drive shaft 16a is pivotably mounted to attachment 36. The shock absorber 16 is to move between a compressed and decompressed position. The shock absorber 16 may include a biasing member (not shown) configured to urge the shock absorber 16 into the decompressed position. For instance, the shock absorber may include a spring, the spring may be internal or external to the shock absorber and when the shock absorber is placed in the compressed position, the spring pushes the legs of the shock absorber into the decompressed position. As the lower strut assembly 14 is pivotably mounted to the upper strut 32, the upper strut 32 presses upwardly against the sleeve 18 urging the sleeve 18 into engagement with the thigh.

Figure 7:
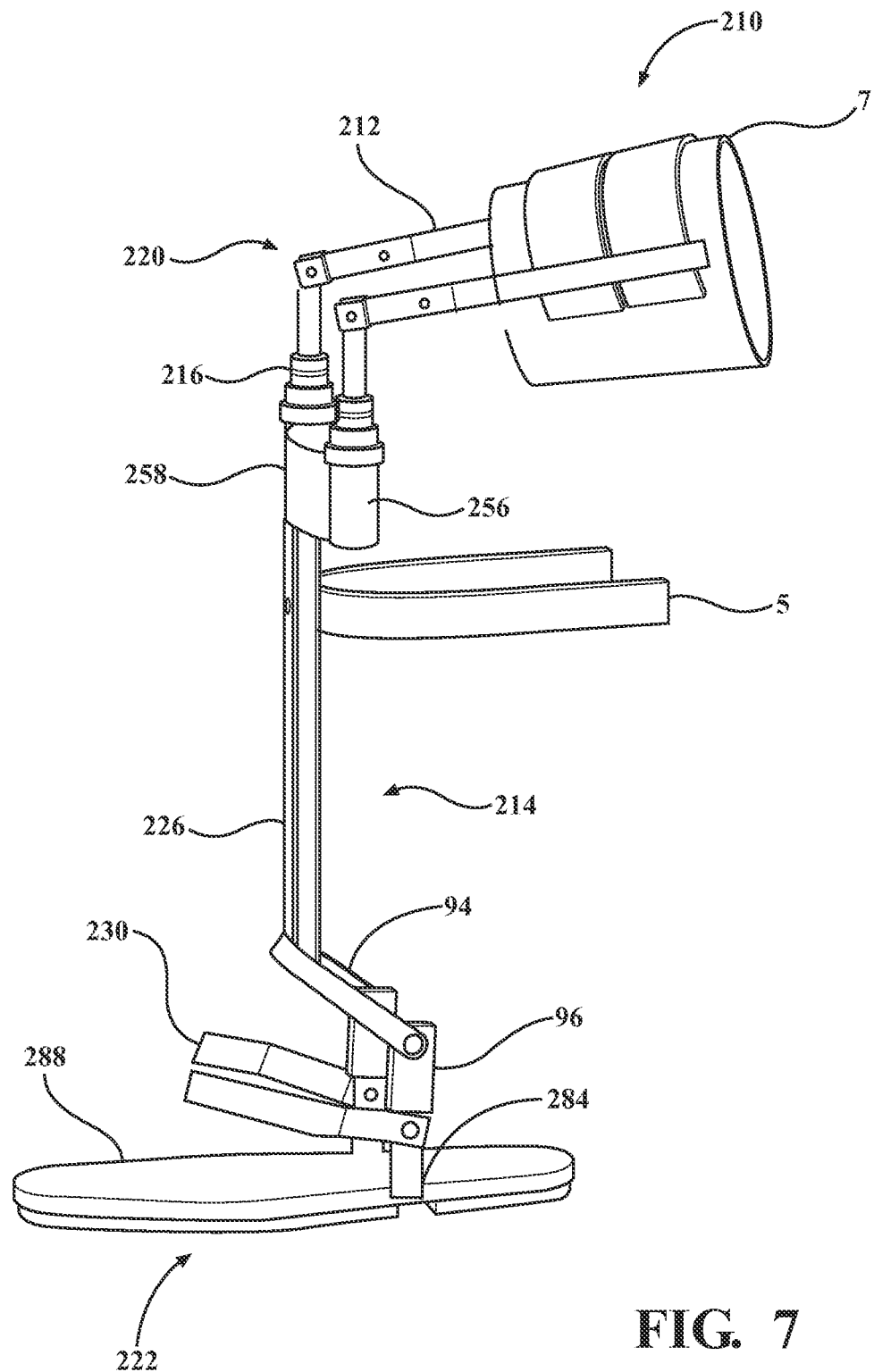
FIG. 7 is an isometric view of the third preferred embodiment of the knee brace with the lower supports in front of the tibia.
Figure 9:
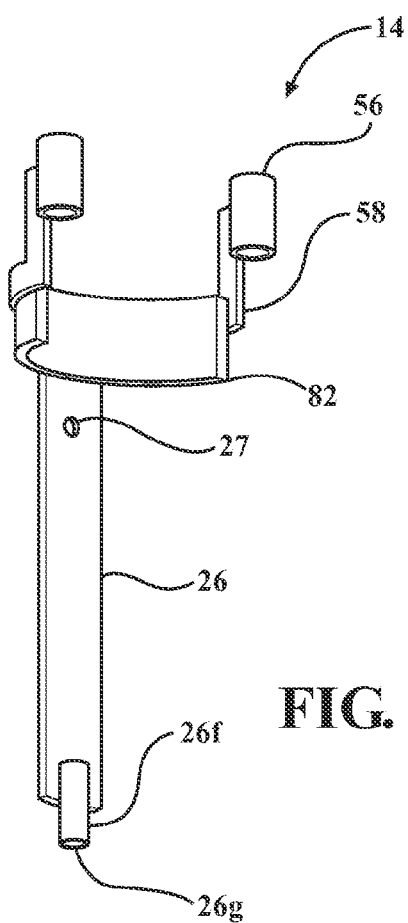
FIG. 9 shows an isometric view of the lower strut assembly shown in FIG. 1.

The lower strut assembly 14 further includes a retaining sleeve 56 configured to hold each of the pair of shock absorbers 16. With reference to FIGS. 4, 7 and 9 the retaining sleeve 56 is a generally cylindrical body having a bore configured to receive the shock absorbers 16 as shown in FIGS. 4 and 7. The lower strut assembly 14 includes a calf support 58 having a semicircular dimension, and a pair of posts 60 mounted to opposing sides of the calf support 58. The calf support 58 is fixedly mounted to a top end of the lower strut 26 by welding or other means of fixed attachment.

Figure 17:
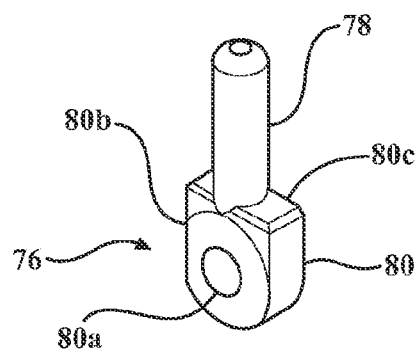
FIG. 17 is an isometric view of the pin assembly.

With reference now to FIGS. 4, 9 and 17, the lower strut 26 may be pivotably mounted to a back end portion of the heel 62 of the shoe sole insert 22. The shoe sole insert 22 includes pin support assembly 64, the pin support assembly 64 includes a base 66 that is generally cross shaped in dimension. The base 66 includes a back support 68 having a pair of supports 70 spaced apart from each other, each support 70 having a hole 70a which are axially aligned with each other. A lower fastener support member 72 may be integrally disposed above the support and include a hole 72a on each end for which the second lower attachment 30 may be mounted. A forward planar member 66a of the base is adapted to be mounted to the shoe sole insert support 74, the shoe sole insert support 74 being adapted to support the foot of a user. The shoe sole insert support 74 includes a heel portion 62 located at the back of the shoe sole insert support 74 and configured to support the heel of a user, as well as a front portion generally dimensioned to support the toes of the user. The forward planar member 66a of the base 66 may be inserted to the heel portion 62 of the shoe sole insert support 74, wherein the back support 68 is exposed and generally orthogonal to the plane of the shoe sole insert support 74.

With reference now to FIG. 17, a pin assembly 76 is provided. The pin assembly 76 includes a pin 78 and is pivotably mounted to the back support 68 of the pin assembly support 64. The pin 78 is fixedly mounted on a pin base 80. The pin base 80 includes a hole 80a defining an opening on opposite sides of the pin base 80. The pin base 80 is disposed between the pair of back supports 70, wherein the hole 80a is aligned with the hole 70a of the support 70 wherein a pin is inserted through holes 80a and 70a so as to pivotably attach the pin base 80 to the insert 22. The lower strut 26 includes a tube 26a configured to engage the pin 78. As shown in the drawings, the pin base is dimensioned so as to be limited in its rotation about pin 171.

With reference first to FIG. 9, a lower strut assembly 14 is provided. The lower strut assembly 14 includes a lower strut 26 having a top end and a bottom end. The lower strut 26 is made of a strong yet light material. The calf support 58 is fixedly disposed on the top end of the lower strut 26 and a tube 26f with an open end 26g is fixedly disposed on the bottom end. The open end 26b is configured to receive the pin 78 and the tube 26a is dimensioned to slidingly engage the pin 78 as shown in FIGS. 4 and 5.

With reference also to FIG. 17, the open end 26b is configured to engage the pin 78 of the pin assembly 76. The shoe insert 22 is thus pivotably attached to the lower strut 26 as the base 66 is fixed within the shoe sole insert 22. The pin 78 is pivotably mounted within the support 70, and the pin base 80 is dimensioned such that the pin 78 has a limited amount of movement around the axis of the clevis pin hole 70a of the support 70.

As shown in FIG. 17, the pin base 80 includes a back wall 80b which is generally planar and abuts against a front surface of the back support 68 so as to limit the rotation of the pin 78. The pin base 80 further includes a shoulder 80c. The shoulder 80c is load bearing and supports the load of the lower strut 26. The bottom end of the pin base 80 is rounded so as to provide for limited rotation of the pin 78.

Figure 8:
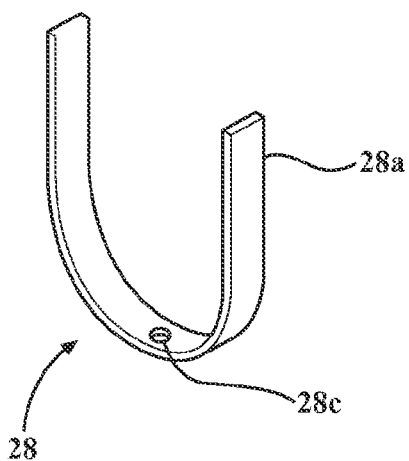
FIG. 8 is an isometric view of the strap used to snug up the lower support assembly of the preferred rear support knee brace to the calf of the individual.

With reference now to FIGS. 4, 5, 9, 18 and 19, the lower strut assembly 14 may further include a first lower attachment 28 and a second lower attachment 30. The first lower attachment 28 is disposed above the second lower attachment 30 and is configured to engage the calf so as to secure the lower strut assembly 14 to the calf. For illustrative purposes the first and second lower attachments 28, 30 are shown as a strap. With reference specifically to FIG. 9, the lower strut 26 includes a hole 27 configured to attach the first lower attachment 28 (shown as a strap). With reference also to FIGS. 4, 5 and 8, a fastener 28c is used to attach the midsection of the first lower attachment 28 to the lower strut 26 through the hole 27. The free ends of the strap 28 may include a fastener 28a such as Velcor® to secure the strap over the calf of the user.

Figure 18:
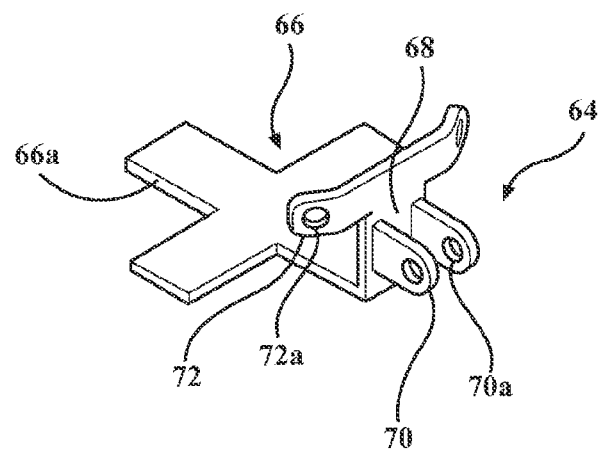
FIG. 18 is an isometric view of the pin support assembly.
Figure 19:
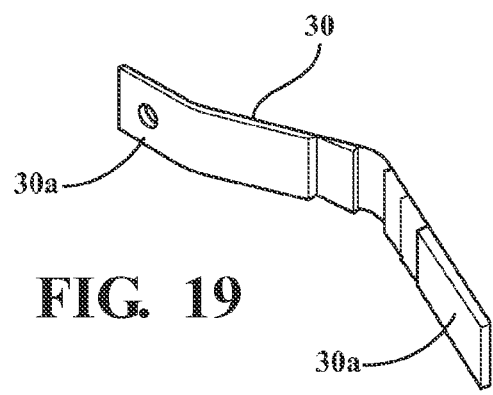
FIG. 19 shows an isometric view of a second lower attachment.

With reference now to FIGS. 4, 5, 18 and 19 the second lower attachment 30 is provided. The second lower attachment 30 is configured to engage the foot of the user so as to secure the shoe sole insert 22 to the foot. With reference specifically to FIG. 18, the pin support assembly 64 of the shoe sole insert 22 is provided. The lower fastener support member 72 is shown as an elongated and planar member disposed along an axis generally orthogonal to the lower strut 26. The lower fastener support member 72 may be integrally formed above the support 70 and includes a pair of holes 72a disposed on respective ends for which the second lower attachment 30 may be mounted.

The second lower attachment 30 is shown as a strap, having a fastener 30a configured to engage a respective hole 72a of the lower fastener support member 72. The fastener 30a is shown as a tab disposed on one end of the second lower attachment 30. The other end of the second lower attachment 30 includes a fastener 30b configured to retain the strap 30 over the foot thereby securing the shoe sole insert 22 to the foot. The straps 30 may be mounted over the ankle of the user to secure the foot to the shoe sole insert 22. It should be appreciated that the straps may be configured such that the free ends of the respective straps 16 are engaged to each other.

Figure 16:
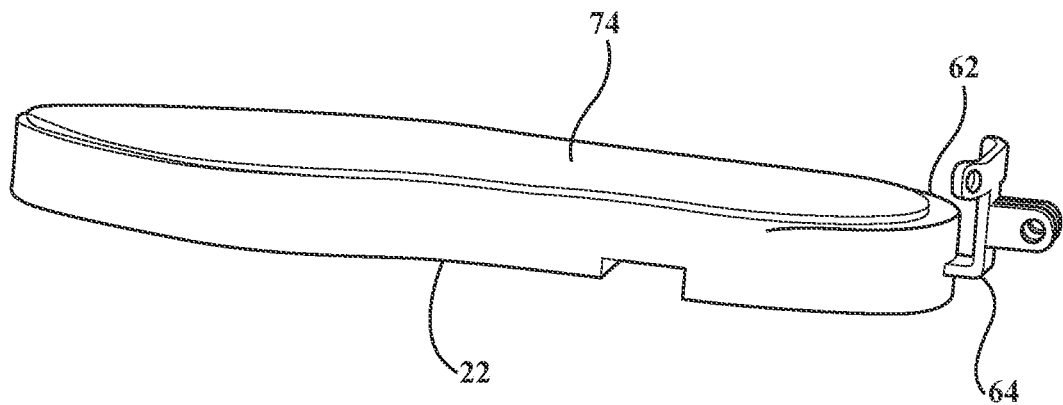
FIG. 16 is an isometric view of the shoe sole insert of FIGS. 4 and 5.

FIG. 4 also shows the insert 22 shaped as the sole of a shoe. The sole represents the position of the foot of the individual and a detailed isometric view of the same sole is shown in FIG. 16. The sole may be made of a customary shoe sole material such as rubber or leather or a synthetic composite material. FIG. 16 shows how the shoe insert 22 made of a strong load bearing material such as a light metal or high density plastic, is to be incorporated in the heel of the sole of the shoe. It is to be inserted in the middle of the heel and fixed in place so that it becomes an integral part of the sole.

FIG. 4 also shows the soft contact liner 82 attached to the lower strut 26 fixedly layered on the calf support 58 depicted in FIG. 9. It should be appreciated that the dimensions of the brace 10 may be customized to the dimensional requirements of individual users so as to maximize the shock absorber impact.

Figure 6:
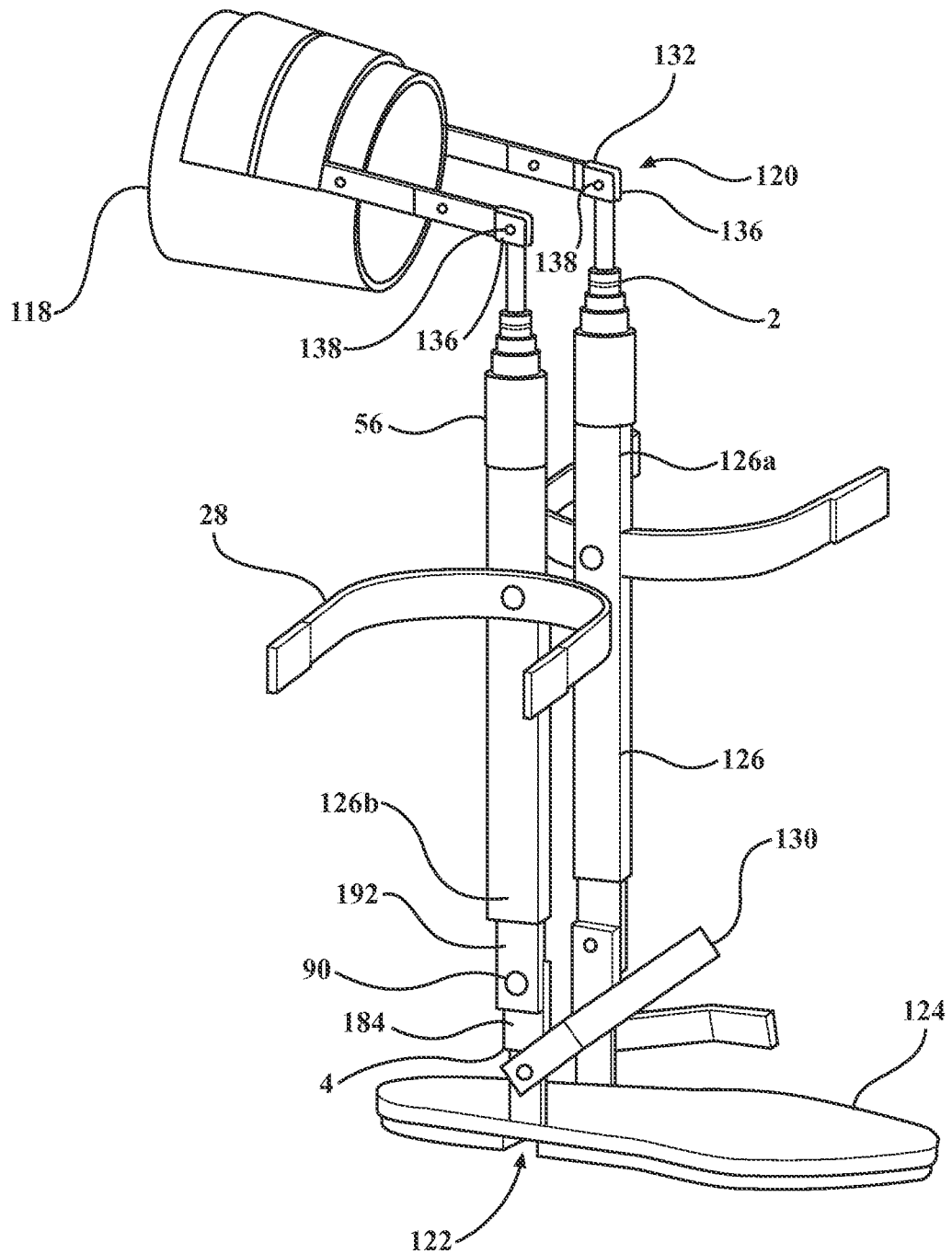
FIG. 6 is an isometric view of the second preferred embodiment of the knee brace showing the lower limb having lateral supports.

With reference now to FIG. 6 a second preferred embodiment of the brace 10, wherein like elements are referenced by like numbers increased by 100, adapted to be used with a shoe sole insert 122 having a pair of upwardly extending arms 84 is provided. The pair of upwardly extending arms 84 is rigidly fixed to the shoe sole insert 122. The shoe sole insert 122 made of a strong load bearing material as described above. Each of the pair of upwardly extending arms 84 is pivotably connected to the lower strut 126. The shoe sole insert 122 includes a base 88, dimensioned to support the foot of a user. In the second embodiment, the upper sleeve assembly 112 is pivotably connected to a pair of shock absorbers 116 in the same manner as described above.

Figure 11:
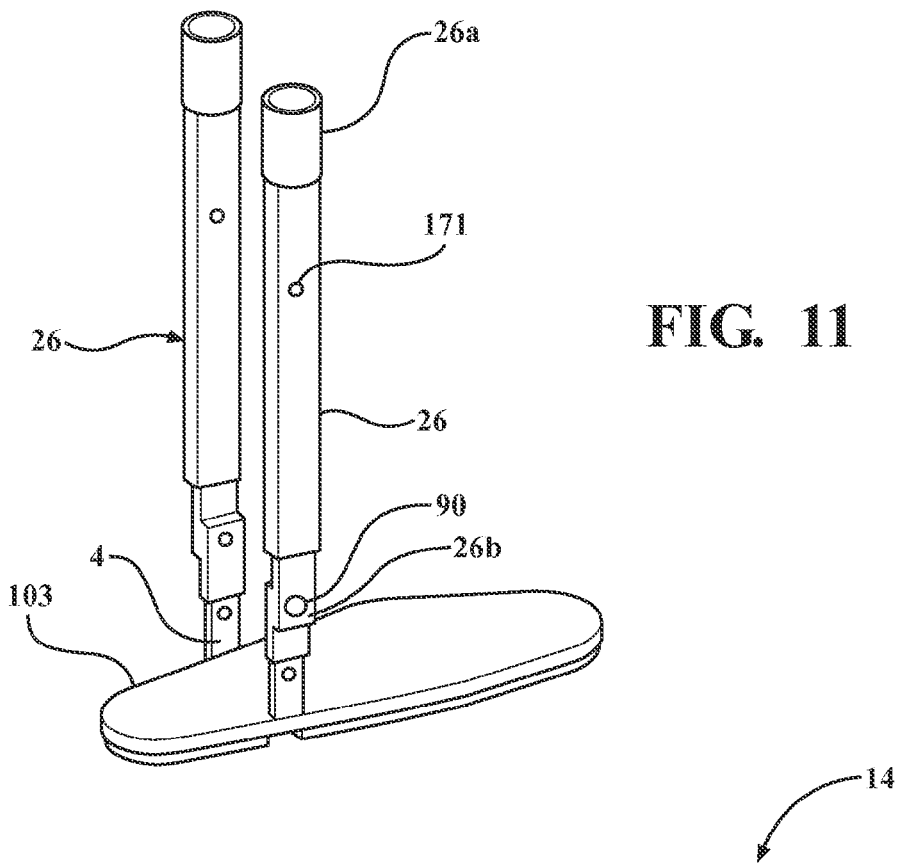
FIG. 11 is an isometric view of the lower strut assembly of FIG. 6.

With reference again to FIG. 6 and also to FIG. 11, the lower strut assembly 114 includes a pair of lower struts 126. The lower struts 126 have a top end 126a and a bottom end 126b. The lower struts 126 are generally axial and are spaced apart from each other so as to be disposed on opposite sides of the calf. The top end 126a of each of the pair of lower struts 126 is mounted to a respective one of the pair of shock absorbers 116. The pair of lower struts 126 include retaining sleeves 156 disposed on the top end 126a. The retaining sleeves 156 are configured to hold the shock absorbers 116 in place. The retaining sleeve 156 may include a threaded bore configured to threadedly engage a threaded body of the shock absorber 116.

With reference again to FIGS. 6 and 11, also to FIG. 20, the bottom end 126b of the lower struts 126 are attached via a pivot pin 90 to the shoe insert 122. An example of the pivot arrangement is shown in FIGS. 6 and 11, wherein the shoe sole insert 122 includes a pair of spaced apart upwardly extending arms 84. The brace 110 is configured to slide on and engage the upwardly extending arms 84. The arms 84 include a hole 84a configured to retain a pivot pin 90. A connecting member 92 (shown in FIG. 6) is pivotably connected to a respective arm 84 via pivot pin 90, and the bottom end 126b of the lower strut 126 may include a slot (not shown) configured to slide on to the connecting member.

Taken into consideration FIGS. 11, and 20, it should be appreciated that the brace 110 of the second preferred embodiment provides for the same pivot point as the brace 10 of the first preferred embodiment. Specifically, the pivot 20, 120 point with respect to the upper sleeve assemblies 12, 112 and the lower strut assemblies 14, 114 of both braces 10, 110 is above the natural pivot point of the knee. However, the pivot points of the shoe inserts 22, 122 with respect to the lower struts 26, 126 is different. Namely, pivot point of the shoe sole insert 122 relative to the lower strut 126 of the second preferred embodiment is above the arch of the foot, as opposed to the first preferred embodiment wherein the pivot point of the shoe sole insert 22 relative to the lower strut 26 is at the heel. Further, the brace 110 of the second embodiment provides for greater lateral stability as there are two lower struts 126 supporting opposite sides of the calf.

Figure 10:
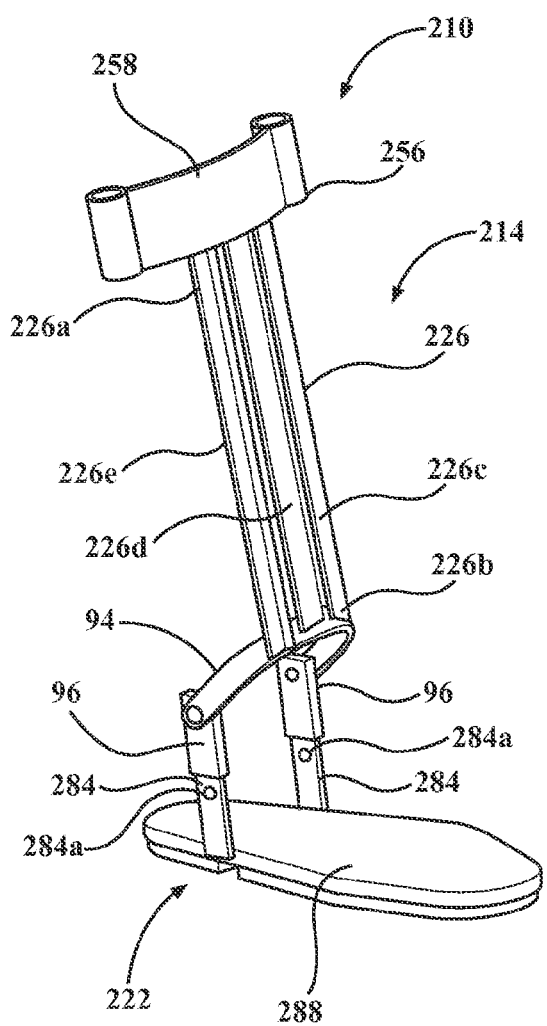
FIG. 10 is an isometric view of the lower strut assembly of FIG. 7.

With reference now to FIGS. 7 and 10 a third preferred embodiment of the brace 10 is provided wherein like elements are referenced by like numbers increased by 200. The brace 210 adapted to be used with a shoe sole insert 222 having a pair of upwardly extending arms 284 is provided. The pair of upwardly extending arms 284 is rigidly fixed to the shoe sole insert 222. The shoe sole insert 222 is made of a strong load bearing material as described above. Each of the pair of upwardly extending arms 284 is pivotably connected to the lower strut 226. The shoe sole insert 222 includes a base 288 dimensioned to support the foot of a user. In the third preferred embodiment, the upper sleeve assembly 212 is pivotably connected to a pair of shock absorbers 216 in the same manner as described above.

In the third preferred embodiment, the knee brace 210 includes a lower strut assembly 214 configured to be positioned in front of the lower leg. An isolated isometric view of the lower strut assembly 214 is also being shown in FIG. 10. The lower strut assembly 214 includes a calf support 258 having a contoured profile, a lower strut 226, and a retainer 94. The lower strut 226 is a generally elongated and rigid member having a top end 226a and a bottom end 226b. Though the lower strut 226 is shown as being three elongated members 226c, 226d, 226e spaced apart and parallel to each other, it should be appreciated that the number of the elongated members is provided for illustrative purposes and is not limiting to the scope of the appended claims.

The lower strut assembly 14 further includes a pair of retaining sleeves 256 are disposed one opposite ends of the calf support 258. The calf support 258 is disposed on the top end 226a of the lower struts 226. The retainer 94 is disposed at the bottom end 226b of the lower strut 226. The retainer 94 is arched so as to go around the ankle. The ends of the retainer 94 are pivotably connected to a respective boot 96 configured to engage a respective upwardly extending arm 284 so as to position the lower strut 226 in front of the calf of the user. The upwardly extending arms 284 may include a hole 284a for which the second lower attachment 230 may be pivotably mounted to so as to secure the foot to the shoe sole insert 222.

With reference now to FIGS. 24-43, a fourth preferred embodiment of the knee brace 10, wherein like elements are referenced with like numbers increased by 300, is provided. The fourth embodiment utilizes the same principal of over-center wherein the first pivot point 320 of the knee brace 310 is displaced above the natural pivot point of the user's knee. It is a further objective of the fourth preferred embodiment of the knee brace 310 to position the shock absorbers 316 so as to not interfere or rub against the leg of the user. It is another object of the fourth preferred embodiment of the knee brace 310 to position the upper struts 332 in alignment with the femur.

FIG. 22 and FIG. 23 show the methodology and design used to enable the overcenter principle to be used in a repeatable and reproducible manner, in the face of individual leg and knee size and shape variations. FIG. 23 shows the individual in the sitting position with 101 representing the thigh, 102 representing the lower leg 105 and the shoe 24. The first pivot point of the linkage is represented by 320 on the upper strut 332 attached to the sleeve 318 wrapped around the thigh 101. A portion of the upper strut 332 is positioned with respect to the center of rotation of the knee 105, such that as the individual stands up the upper portion of the upper strut 332 rotates along with the center of rotation of the knee and the pivot point 320 effectively travels a distance represented by "d". As long as this movement is repeatably available to actuate the shock absorbers 316, the brace 310 can be adjusted to provide the desired force response in a reproducible and repeatable manner from day to day and from individual to individual.

Another aspect of this design is that when the upper struts 332 are aligned with the axis of the thigh and the pivot point is positioned as described with respect to the center of rotation of the knee, the lateral forces experienced by the device are reduced to an acceptable level.

Figure 24:
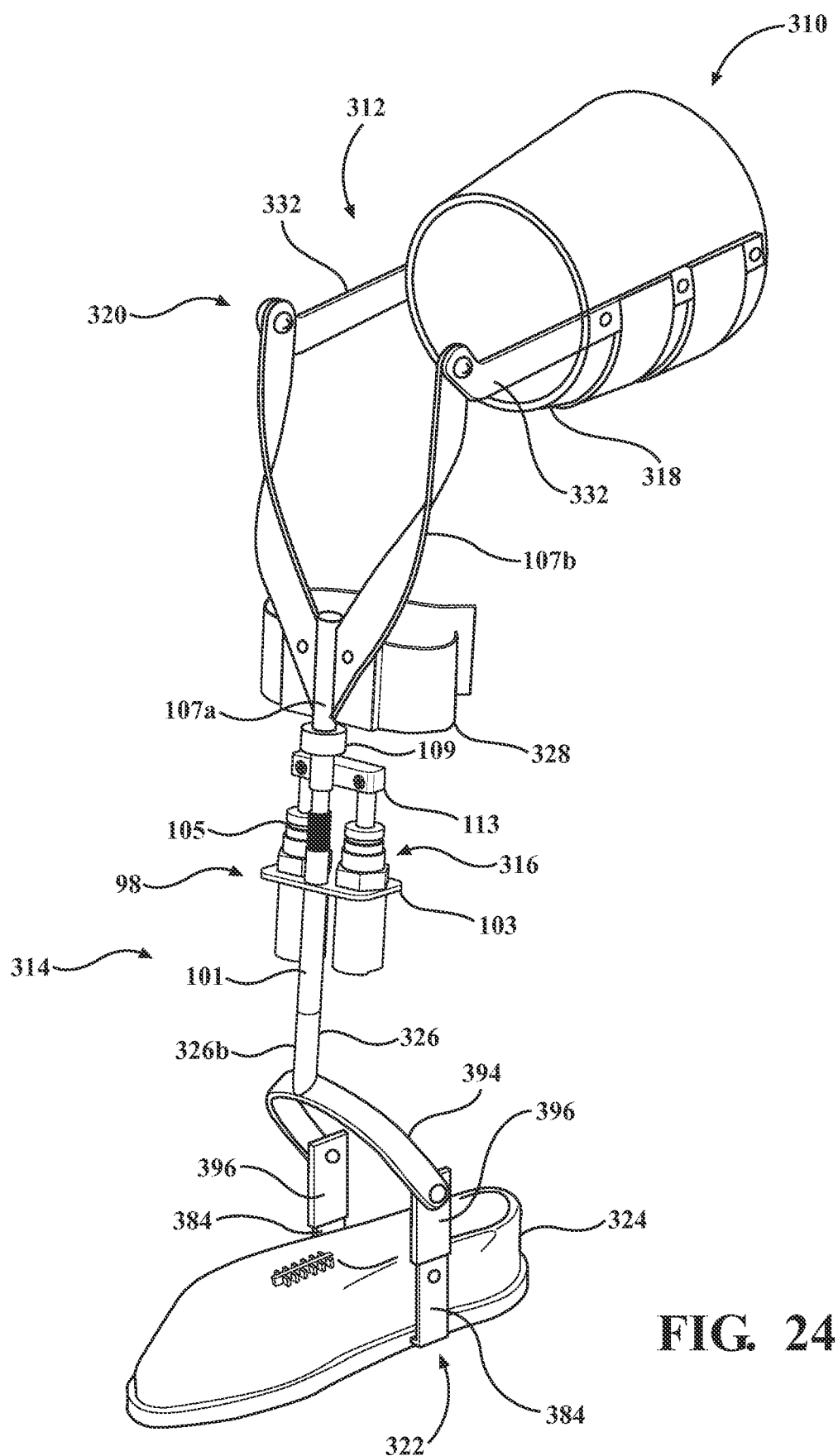
FIG. 24 shows an isometric view of the fourth preferred embodiment of the knee brace.

FIG. 24 shows an isolated isometric view of the preferred exoskeletal, load bearing, shock absorbing knee brace 310 as it would be with the individual in the seated position. The knee brace 310 is configured to be worn on a leg and designed to support a knee principally by reducing the load on the knee and absorbing peak shock loads when the leg is articulated. The knee brace 310 is coupled to both a thigh and a calf of a user. The knee brace 310 includes an upper sleeve assembly 312 having a sleeve 318 configured to engage the thigh.

The knee brace 310 further includes a lower strut assembly 314 configured to engage the calf, and a pair of shock absorbers 316. Each of the shock absorbers 316 are moveable between a compressed and decompressed position. The pair of shock absorbers 316 is mechanically connected to both the upper sleeve assembly 312 and the lower strut assembly 314. The upper sleeve assembly 312 and lower strut assembly 314 are pivotable relative to each other about a first pivot point 320. The first pivot point 320 is above and forward of a pivot point of a bent knee so as to actuate the pair of shock absorbers 316 to the compressed position when the upper sleeve 318 is pivoted relative to lower strut assembly 314 by the articulation of the leg, the knee brace 310 absorbing the shock imparted on the knee.

Figure 28:
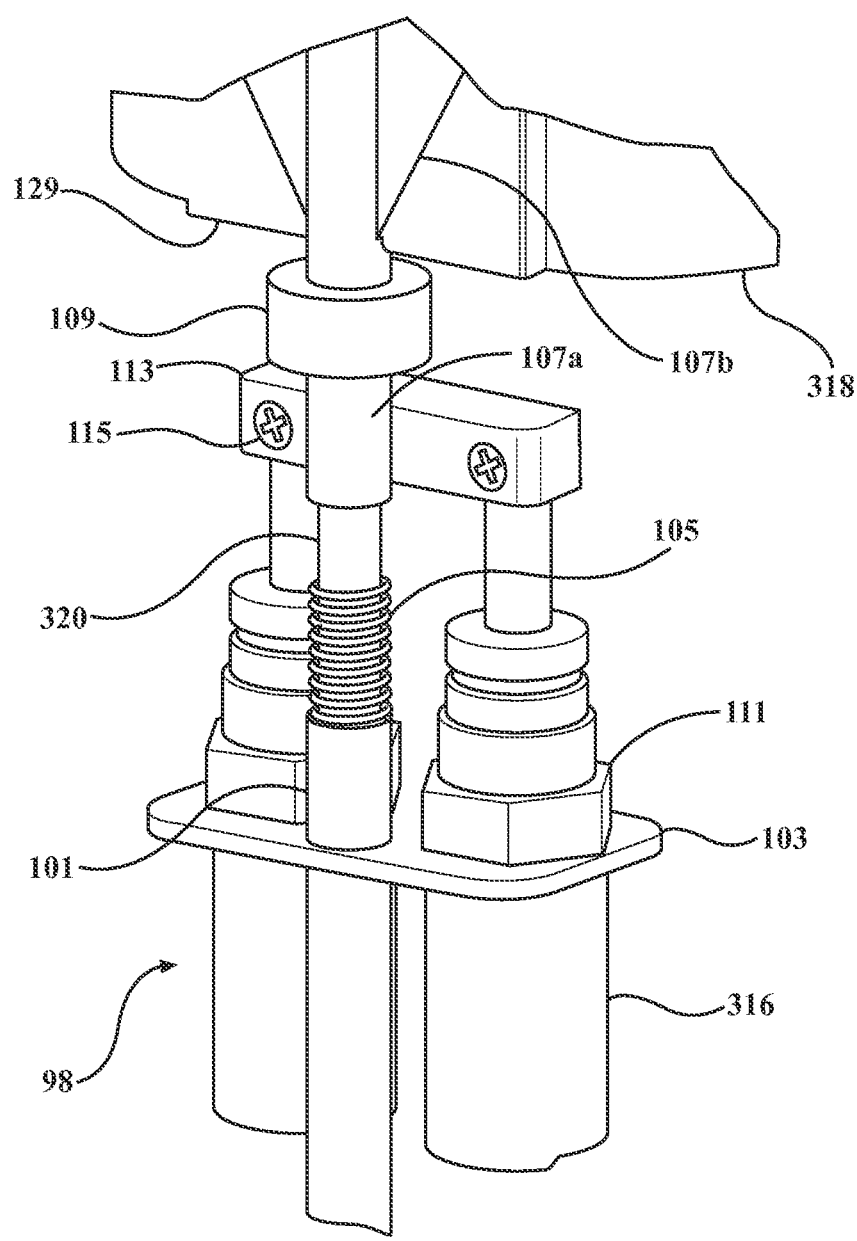
FIG. 28 is a perspective view of a shock absorber support assembly.
Figure 29:
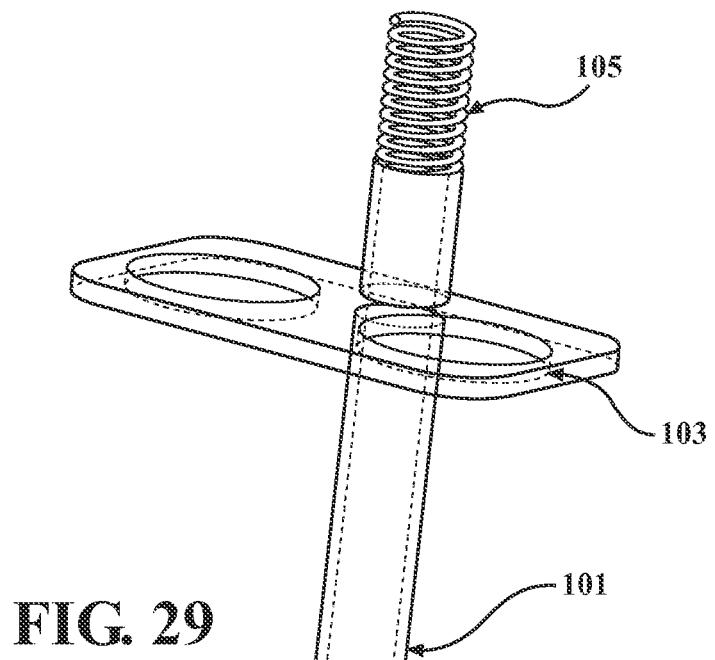
FIG. 29 is a perspective view a bracket and the tube of the shock absorber support assembly.
Figure 30:
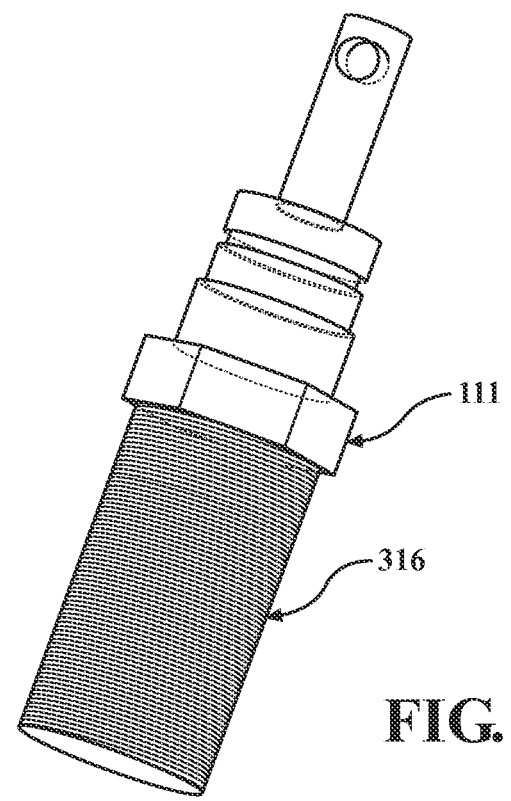
FIG. 30 is an isolated isometric view of a shock absorber.

With reference again to FIG. 24, and also to FIGS. 28, 29 and 30, the lower strut assembly 314 further includes a shock absorber support assembly 98. The shock absorber support assembly 98 includes a tube 101, a bracket 103, a biasing member 105, and a Y-shaped member 107.

The lower strut assembly 314 further includes a lower strut 326. The lower strut 326 is a generally elongated and rigid member having a top end opposite a bottom end. The tube 101 is dimensioned to cover a bottom portion of the lower strut 326 wherein a top end of the lower strut 326 is exposed. The biasing member 105 is disposed on a top end of the tube 101.

Figure 25:
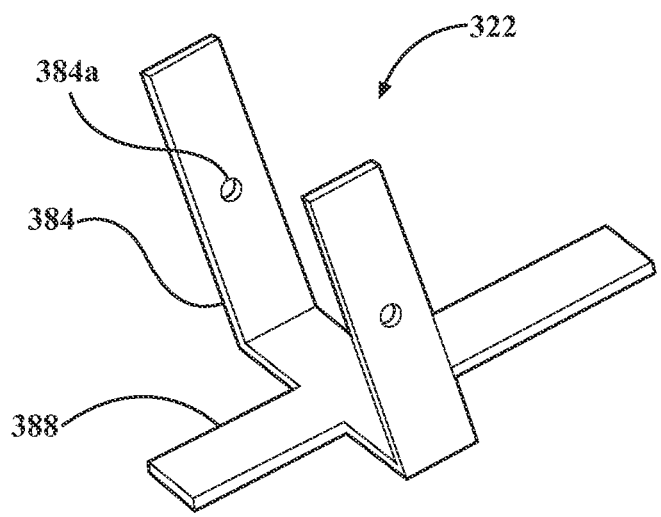
FIG. 25 is an isometric view of the shoe sole insert of FIG. 24.
Figure 26:
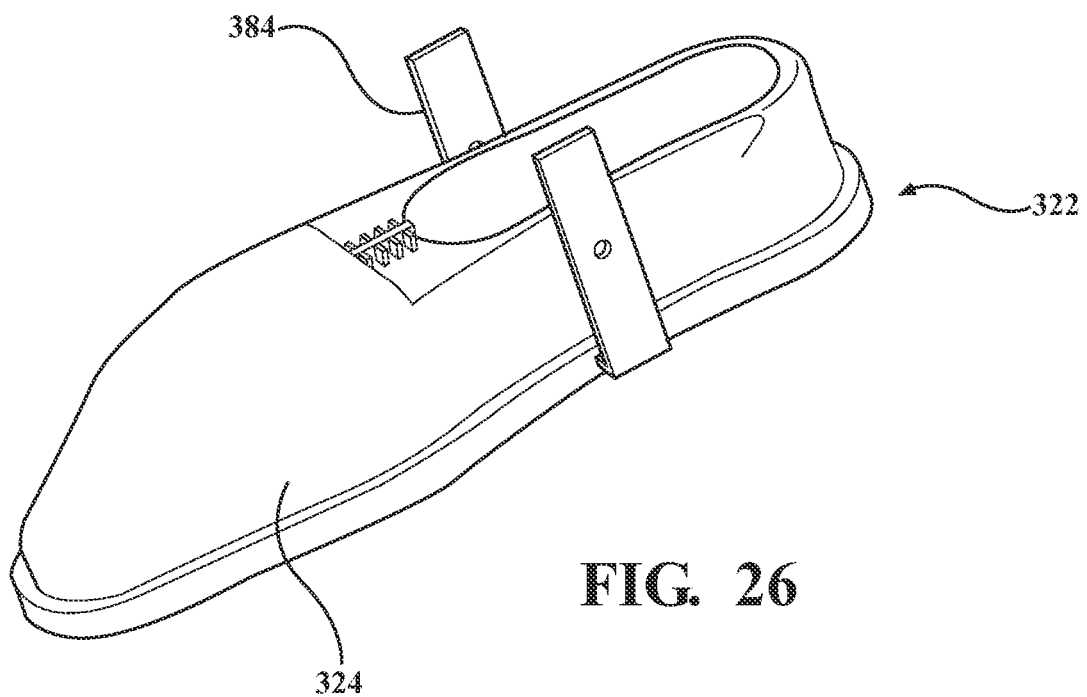
FIG. 26 is perspective view of the shoe sole insert of FIG. 25 incorporated in a shoe.

With reference now to FIGS. 24, 25, and 26 the knee brace 310 may further include a load bearing shoe sole insert 322 configured to be positioned within a shoe 324 of a user, the load bearing shoe sole insert 322 including a base 388 configured to support the foot and pivotably attached to the bottom end of the lower strut 326. The lower strut assembly 314 further includes a retainer 394 disposed on a bottom end 326b of the lower strut 326. The load bearing shoe insert 322 includes a pair of upwardly extending arms 384 disposed on opposite sides of the base 388. The pair of upwardly extending arms 384 are rigid and generally orthogonal to the base 388. The ends of the retainer 394 are pivotably mounted to a respective pair of upwardly extending arms 384 so as to position the lower strut 326 in front of the calf of the user. The retainer 394 is an arched member and further includes a pair of boots 396 pivotably mounted to opposing side ends of the retainer 394, each of the boots 396 includes a bore 396a disposed at the bottom end of a respective boot 396. The bore 396a is dimensioned to sliding engage a respective pair of upwardly extending arm 384. Accordingly, the boot 396 is detachably engaged with a respective one of the pair of upwardly extending arms 384.

The bracket 103 is fixedly mounted to the tube 101 and is configured to hold the pair of shock absorbers 316. The bracket 103 is shown as a generally planar member with a pair of openings dimensioned to fit a bottom end of the shock absorber 316. The bracket 103 is mounted to the tube 101 so as to position the shock absorbers 316 in front of a tibia.

Figure 31:
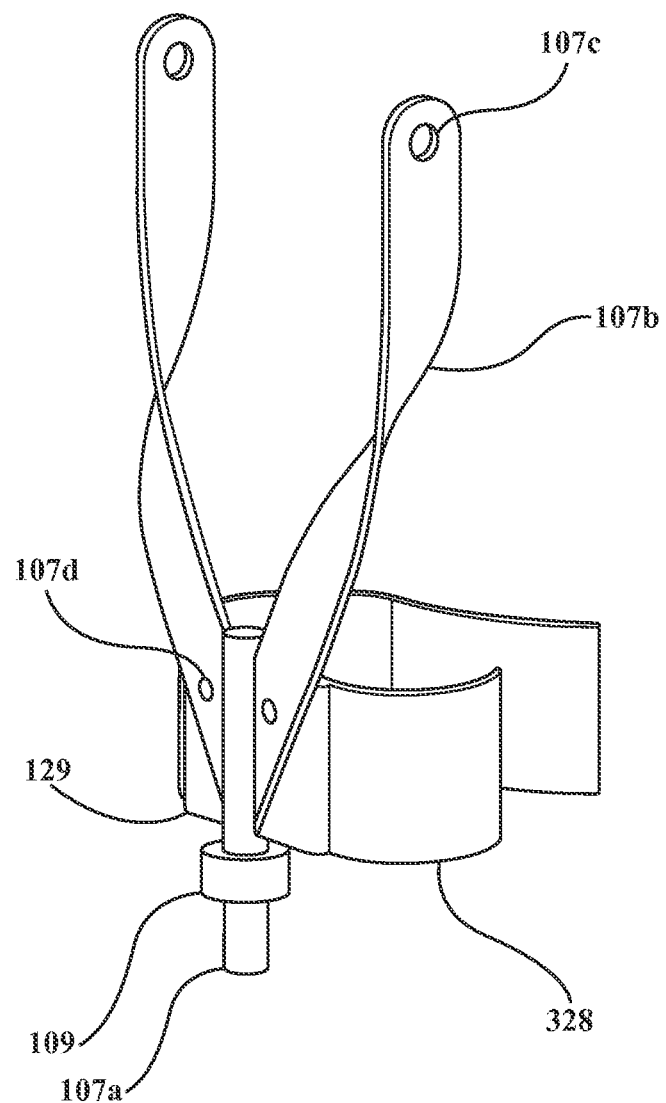
FIG. 31 shows an isometric view of the Y-shaped member.

With reference again to FIG. 24 and also to FIG. 31, an illustrative view of the Y-shaped member 107 is provided. The Y-shaped member 107 includes a stem 107a and a pair of prongs 107b extending from the stem 107a. The stem 107a is a generally rigid and cylindrical member. A collar 109 is fixedly mounted onto the stem 107a and generally delineates a top portion of the stem 107a from a bottom portion of the stem 107a.

The prongs 107b are shown as a generally elongated and planar member, each disposed on opposite sides of the stem 107a and extend away from each other so as to provide space for a bent knee. The ends of the prongs 107b are pivotably mounted to the upper sleeve assembly 312. The prongs 107b may include a twist, wherein one end of the prong is twisted about an axis of the body of the prong. The bottom end of the stem 107a includes a bore 107d dimensioned to engage the top end 326a of the lower strut 326 wherein the shock absorbers 316 and biasing member 105 are operative to urge the stem 107a upwards relative to the bottom end 326b of the lower strut 26.

The person who is to wear the brace 310 is not shown in the view but it can be seen that the individual would lace on the shoes 324, engage the extending arms 384 of the shoe insert 322 with the boots 396 pivotally mounted on the retainer 394. The individual would proceed to tighten the first lower attachment 328 around his calf just below the knee. At this point he would roll the sleeve 318 around his thigh and wrap it snug tight with the fastening device 373, shown as two straps provided with Velcro fasteners. The adjustments available to the individual will be described at a later stage, so at this point the individual knows that the device has been adjusted to his particular requirements.

It is noted that has he stands up the Y-shaped member 107, pivotally connected to the upper struts 332 which are attached to sleeve 318, slides down on the lower strut 326 that is fixedly mounted to the retainer 394. The Y-shaped member 107 is designed to rotate freely and move up and down the top end portion of the lower strut 326 so as not to restrict the angular movement of the foot of the individual.

Depending upon the adjustments, at some point before the individual is fully standing, the Y-shaped member 107 starts making contact with the shock absorber 316, which is positioned in front of the tibia minimizing the potential for interference with the other leg or the even the device on the other leg, should the individual require a device on each of his legs.

With reference again to FIG. 28 we can see the shock absorbers 316 fixedly mounted on bracket 103 such that the nut 111 and the threads on the body of the shock absorber 316 can be used to adjust the axial position of the shock absorber 316 as required. The detailed view of the shock absorber 316 is also shown in FIG. 30.

FIG. 29 provides an isolated view of the tube 101, with the biasing member 105 mounted to a top end of the tube 101 and the bracket 103 fixedly mounted to the tube 101. The tube 101 is dimensioned to provide a close fit with lower strut 326 mentioned earlier. The shock absorbers 316 are connected in a load bearing manner by a bar 113 (shown in FIGS. 28 and 39) held in place with screws 115. Even though these shock absorbers 316 are provided with internal return springs an additional biasing member 105 external to the lower strut 326 is provided to help keep the sleeve 318 pushed up against the thigh and with additional static load support.

FIG. 28 taken together with FIG. 24 show the lower strut 326 on which the shock absorber 316 is positioned in a fixed manner by the bracket 103 so that any force exerted on bar 113 can be transferred to the ground via the lower strut 326, the retainer 394 and the shoe 324. The lower end of the Y-shaped member 107 can be seen coaxial to the lower strut 326 and free to move up and down within the constraints provided. The collar 109 can be moved and locked in position on the lower end of the Y-shaped member 107, and it is this collar 109 that engages the bar 113 as the individual walks or runs and transfers the load from the downwardly projecting collar 109 onto the bar 113.

Figure 32:
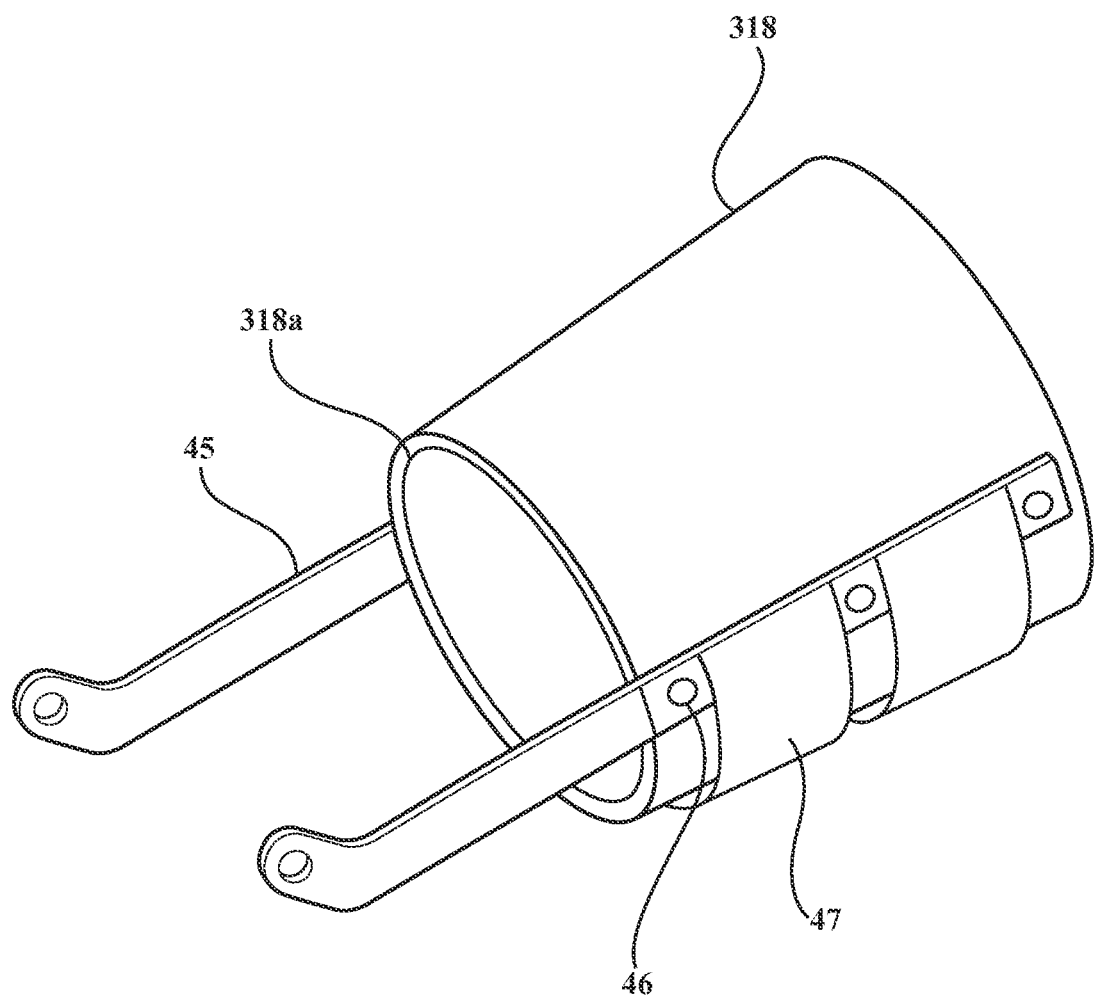
FIG. 32 is a perspective view of the upper sleeve assembly of the fourth preferred embodiment.
Figure 33:
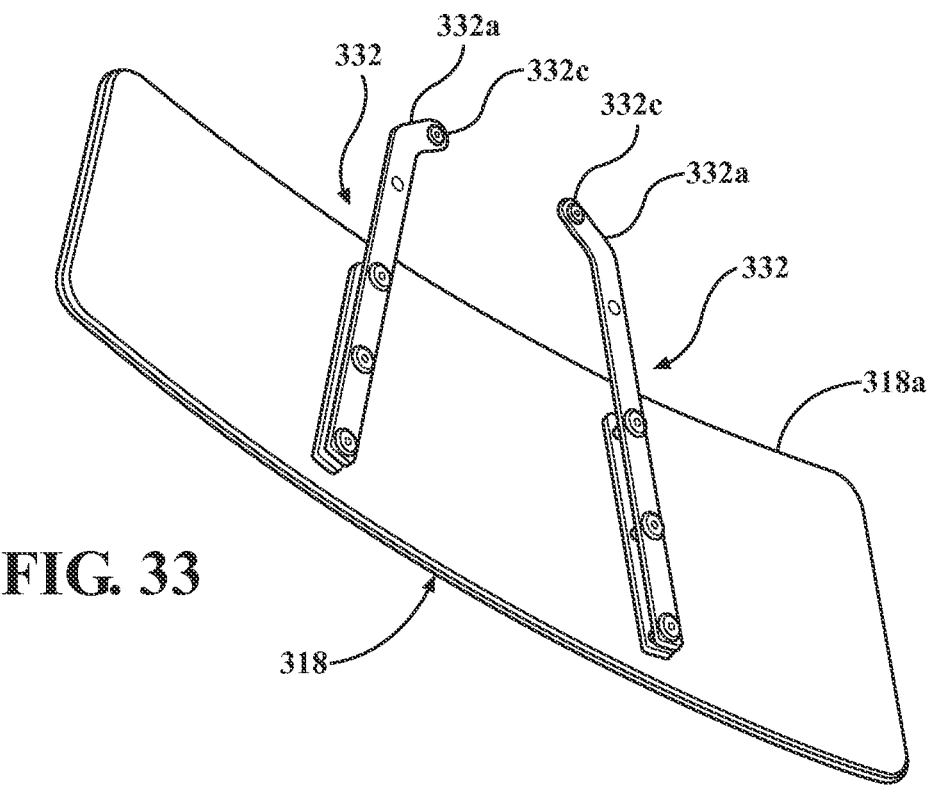
FIG. 33 is a perspective view of the sleeve of FIG. 32 laid flat.
Figure 34:
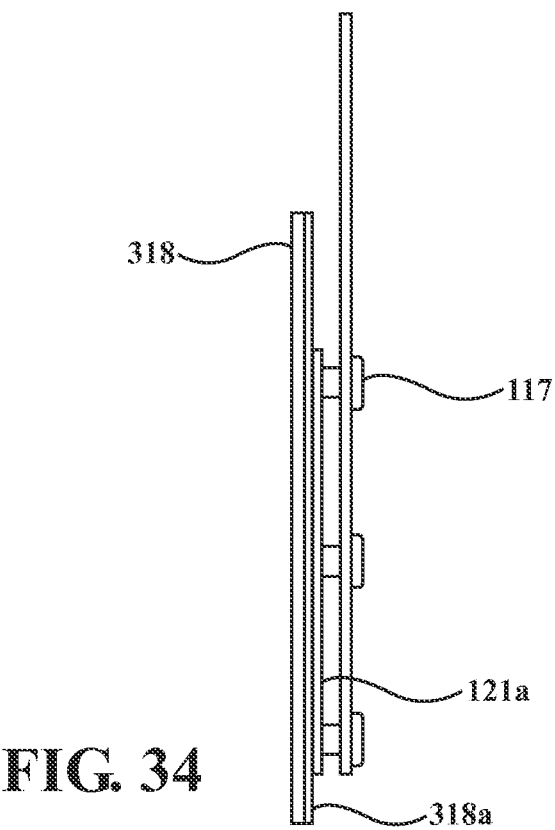
FIG. 34 is an end view of the same sleeve depicting the spacing allowed for the straps used to fasten the sleeve in place.
Figure 35A:
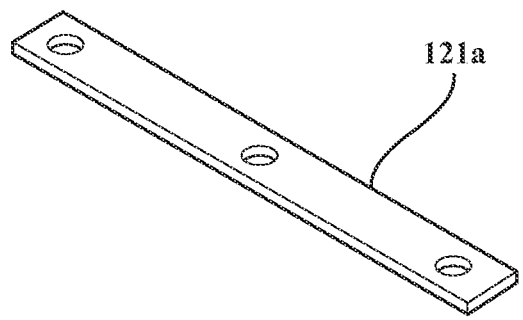
FIG. 35a is an isolated view of one of the spacers.
Figure 35B:
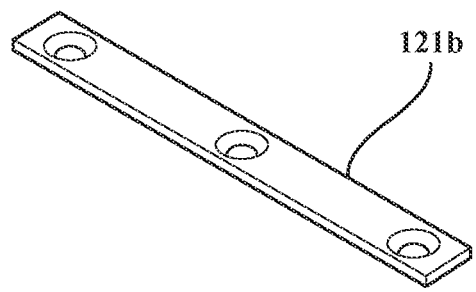
FIG. 35b is an isolated view of the other of the spacers.
Figure 36:
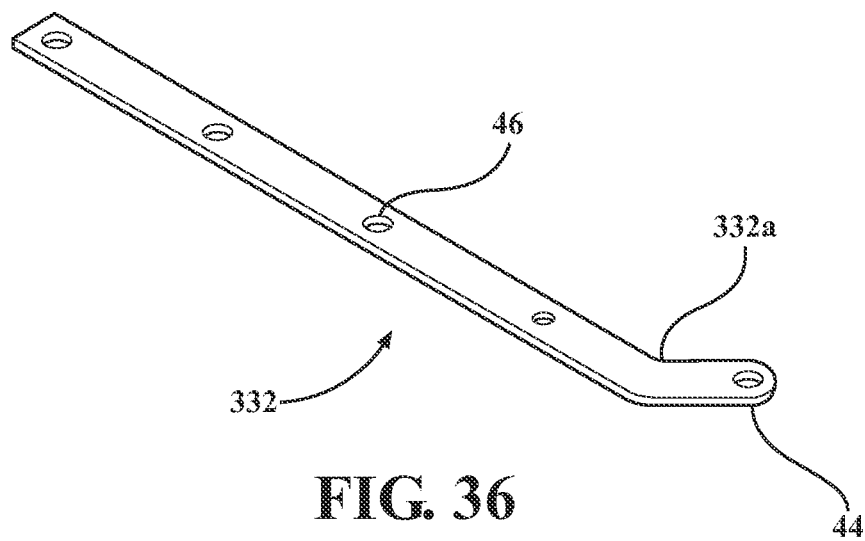
FIG. 36 is an isolated view of an upper strut.
Figure 37:
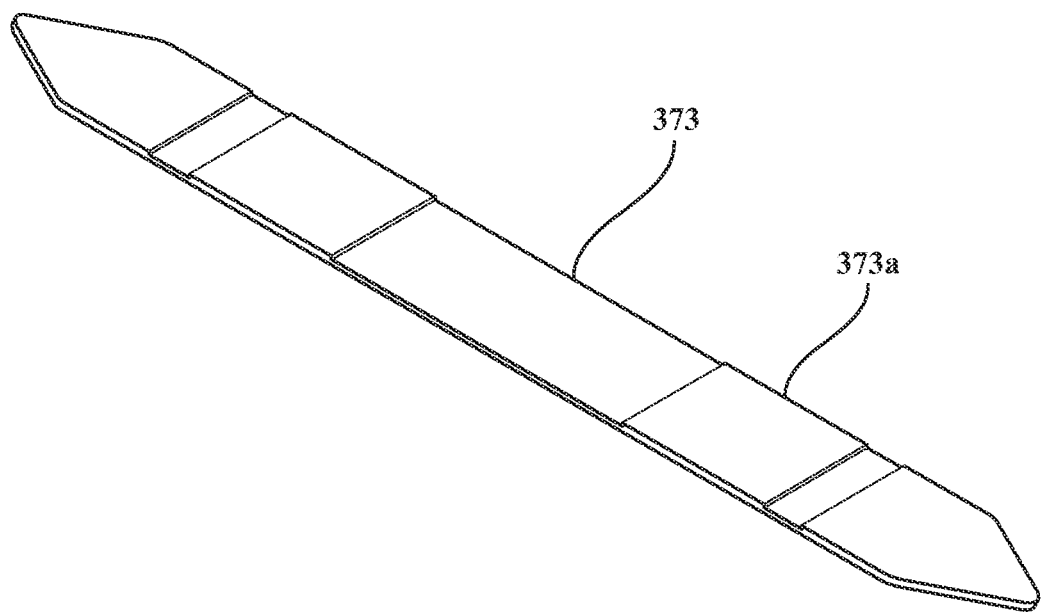
FIG. 37 is an isolated view of the fastening device for securing the sleeve.
Figure 43:
FIG. 43 is a perspective view of a screw.

FIGS. 32 through 37 and 42-43 depict the thigh sleeve 318 and its components. FIG. 33 shows the construction technique of one preferred design. The sleeve 318 is made out of a strong yet flexible material and may include an inner liner 318a that comes in contact with the skin and accordingly made of non-allergenic strong and soft material designed for user comfort. FIG. 33 also depicts the construction technique used to attach the upper struts 332 also shown in detail in FIG. 36. The upper struts 332 include an elongated body and a bottom end 332a which is angled relative to the elongated body. The bottom end 332a may be angled 45 degrees relative to the axis of the upper elongated body 332b of the upper strut. The bottom end 332a includes a hole 332c for pivotable connection to the prongs 407b. Connector nut 117 shown in FIG. 42 and screws 119 shown in FIG. 43 are used to assemble the sleeve 318 and the upper struts 332 using the spacer 121a, and retaining bracket 121b as shown in the end view presented in FIG. 34 so that the straps 373 built with Velcro fasteners 373a can be used to retain the rolled up sleeve 318 as shown in FIG. 32.

Turning our attention to FIGS. 25 and 26 we see the shoe insert 322. The shoe insert 322 includes a pair of upwardly extending arms 384. The upwardly extending arms 384 are also provided with threaded holes 384a for use with additional support straps in case those are desired for extra active applications. FIG. 26 depicts a shoe 24 with the insert 322 made an integral part such that only the upwardly extending arms 384 are visible and available to support the knee brace 310.

Figure 27:
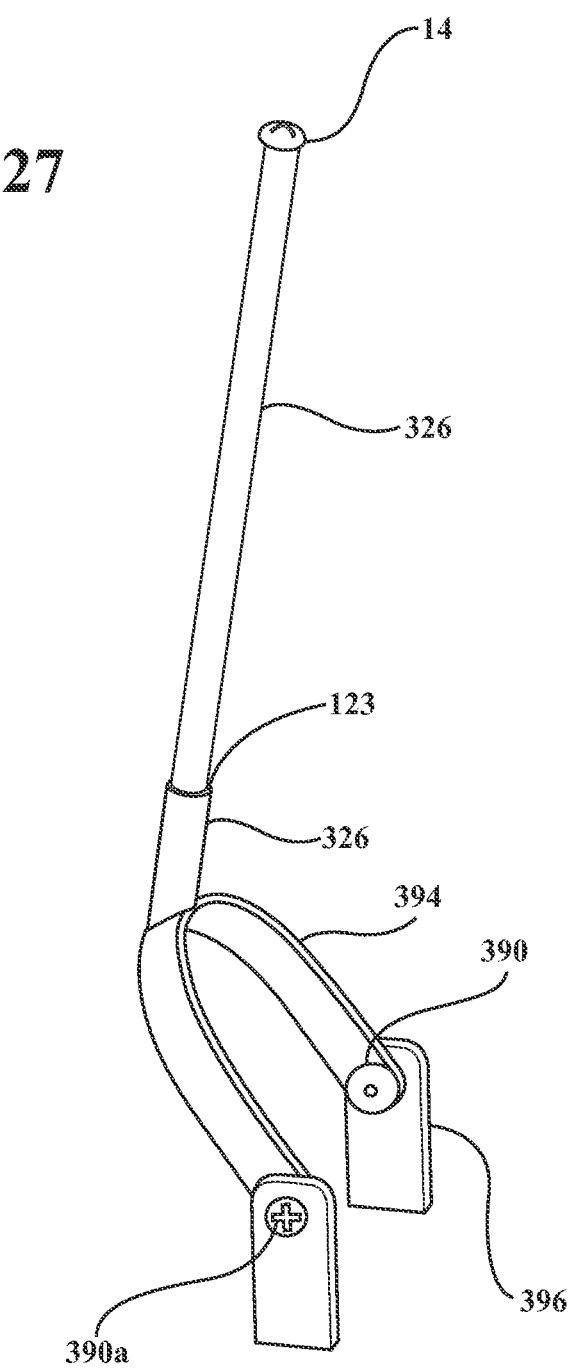
FIG. 27 is a perspective view of the lower strut assembly of FIG. 24.

FIG. 27 shows a subassembly of the lower strut assembly 314, with the lower strut 326 made integral to the retainer 394. The boots 396 designed to closely fit over the extending arms 384 of the shoe sole insert 322 described above are pivotally attached to the ends of the retainer 394 using pivot pin 390 secured within a hole via fastener 390a. The design of this subassembly supports the objective of providing freedom of movement along all axes. The lower strut 326 includes a shoulder 123 which is configured to support the shock absorber support assembly 98, and fastener 125 is configured to retain the lower strut 326 within the stem 107a of the Y-shaped member 107.

FIG. 31 depicts an isometric view of the Y-shaped member. The prongs 107b include holes 107c disposed adjacent the distal end. The prongs 107b are pivotally connected to the upper struts 332 inserting fasteners, such as nut 117 and screw 115, through holes 107c and holes 332c of the bottom end 332a of the upper strut 332. The lower end of the prongs 107b are fixedly connected by welding to the stem 107a. The stem 107a is tubular and configured to freely move up and down the upper portion of the lower strut 326 described above. The collar 109 can be locked in a given position on the stem 107a, as required, by using the set screw 127 shown in FIG. 41.

The collar 109 makes contact with the shock absorber support assembly 98 and provides the required shock absorber actuation movement. As the stem 107a slides up and down the upper portion of the lower strut 326, the end of the stem 107a comes in contact with the spring 105. The dimensions of stem 107a and the upper portion of the lower strut 326 are such that the spring 105 bottoms up before the shock absorber 316 reaches the bottom of the stroke. This can also help maximize load transfer through the brace 310 bypassing the knee joint at the bottom of the stroke.

Figure 38:
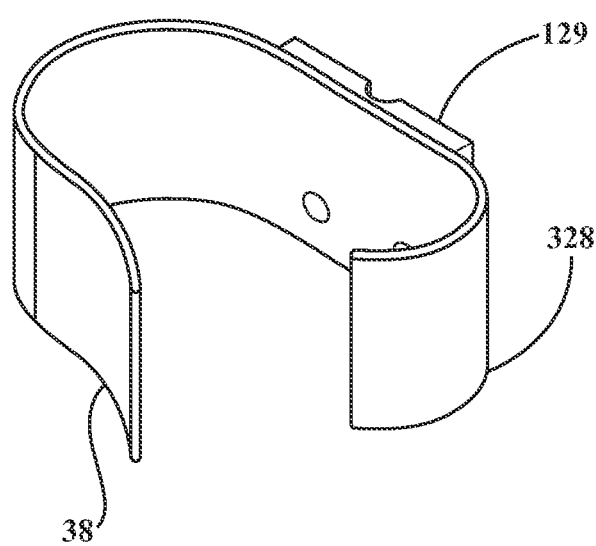
FIG. 38 is a perspective view of the first lower attachment used to fasten the Y-shaped member to the calf.
Figure 39:
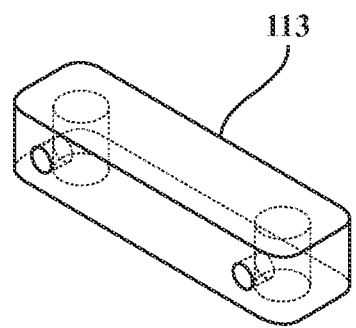
FIG. 39 is an isometric view of the bar used to connect the two shock absorbers.
Figure 40:
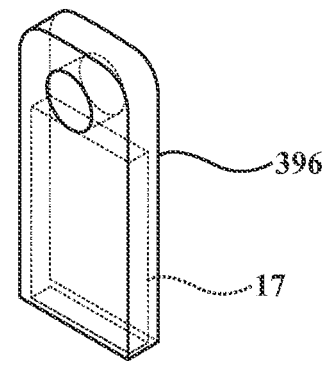
FIG. 40 shows an isometric view of the boots.
Figure 41:
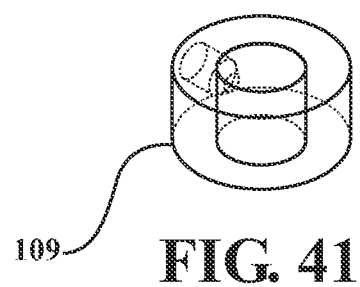
FIG. 41 is an isolated view of the collar that is attached to the Y-shaped member.
Figure 42:
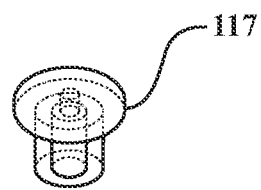
FIG. 42 is an isolated view of a connector nut configured to receive the screw shown in FIG. 43.

With reference again to FIG. 31 and also now to FIG. 38, the shock absorber support assembly 98 may further a first lower attachment 328. The first lower attachment 328 is configured to engage the calf so as to secure the lower strut assembly 314 and the shock absorber support assembly 98 to the calf. With reference again to FIG. 38, the first lower attachment 328 is shown as a strap. The strap 328 may be mounted to the Y-shaped member 107 with the spacer 129 using the holes 107d and fasteners 115 and is configured to allow the user a comfortable, repetitively accurate connection. With reference again to FIG. 38, the strap 328 may include a fastener 328a such as Velcro.

With reference now to FIGS. 44-68, a fifth preferred embodiment of the knee brace 410, wherein like elements are referenced with like numbers increased by 400, is provided. The fifth preferred embodiment utilizes the same principal of overcenter wherein the pivot point of the knee brace 410 is displaced above the natural pivot point of the user knees. It is a further objective of the fifth preferred embodiment of the knee brace 410 to provide a streamlined shock absorber that also provides substantial and very desirable weight reduction. Further, the fifth preferred embodiment provides a knee brace 410 wherein when the upper struts 432 are aligned with the axis of the thigh and the pivot point is positioned as described with respect to the center of rotation of the knee, the lateral or transverse forces experienced by the device at the sleeve 418 are minimized.

Figure 44:
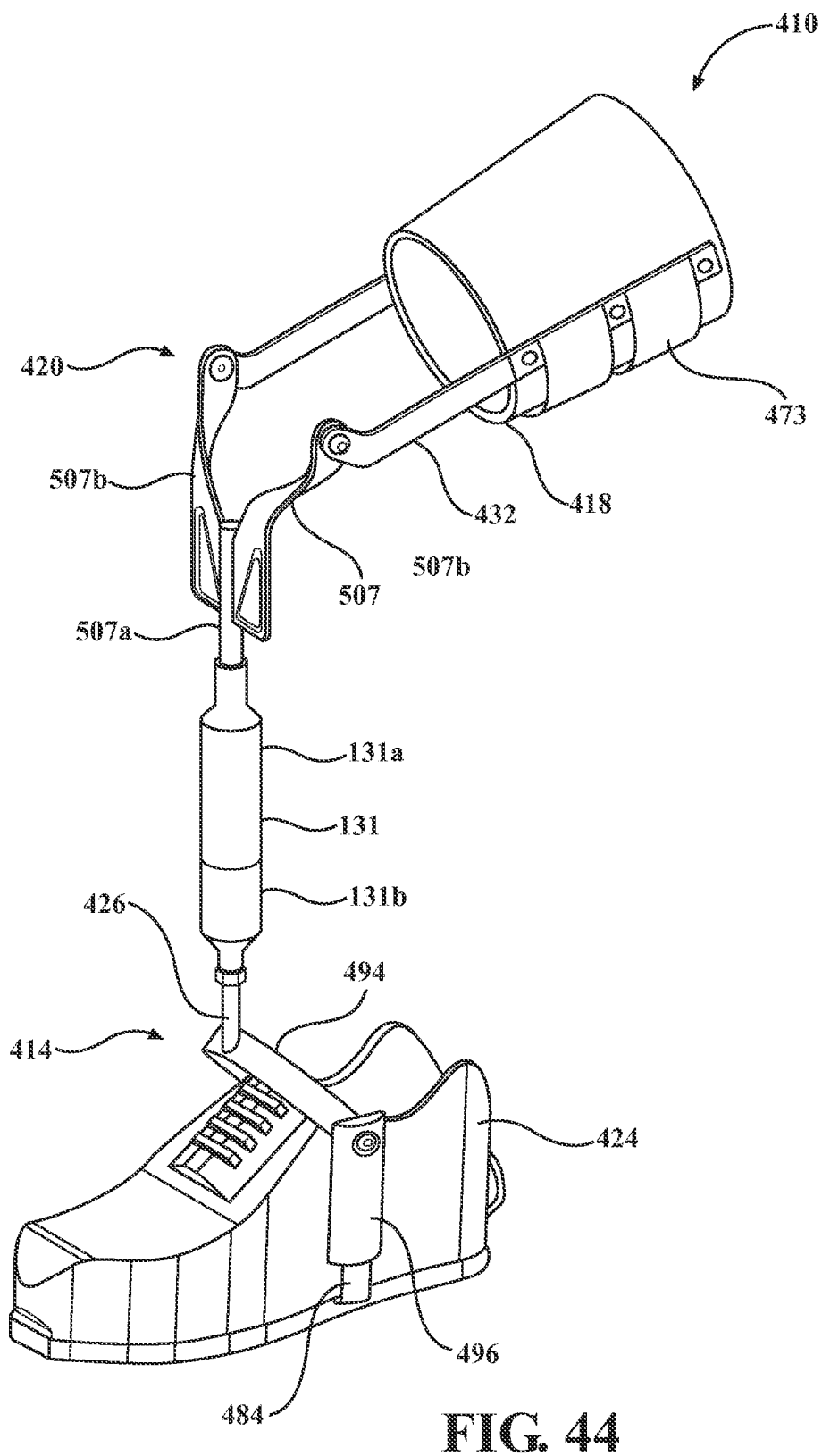
FIG. 44 is an isometric view of the fifth preferred embodiment of the knee brace.
Figures 49, 50:
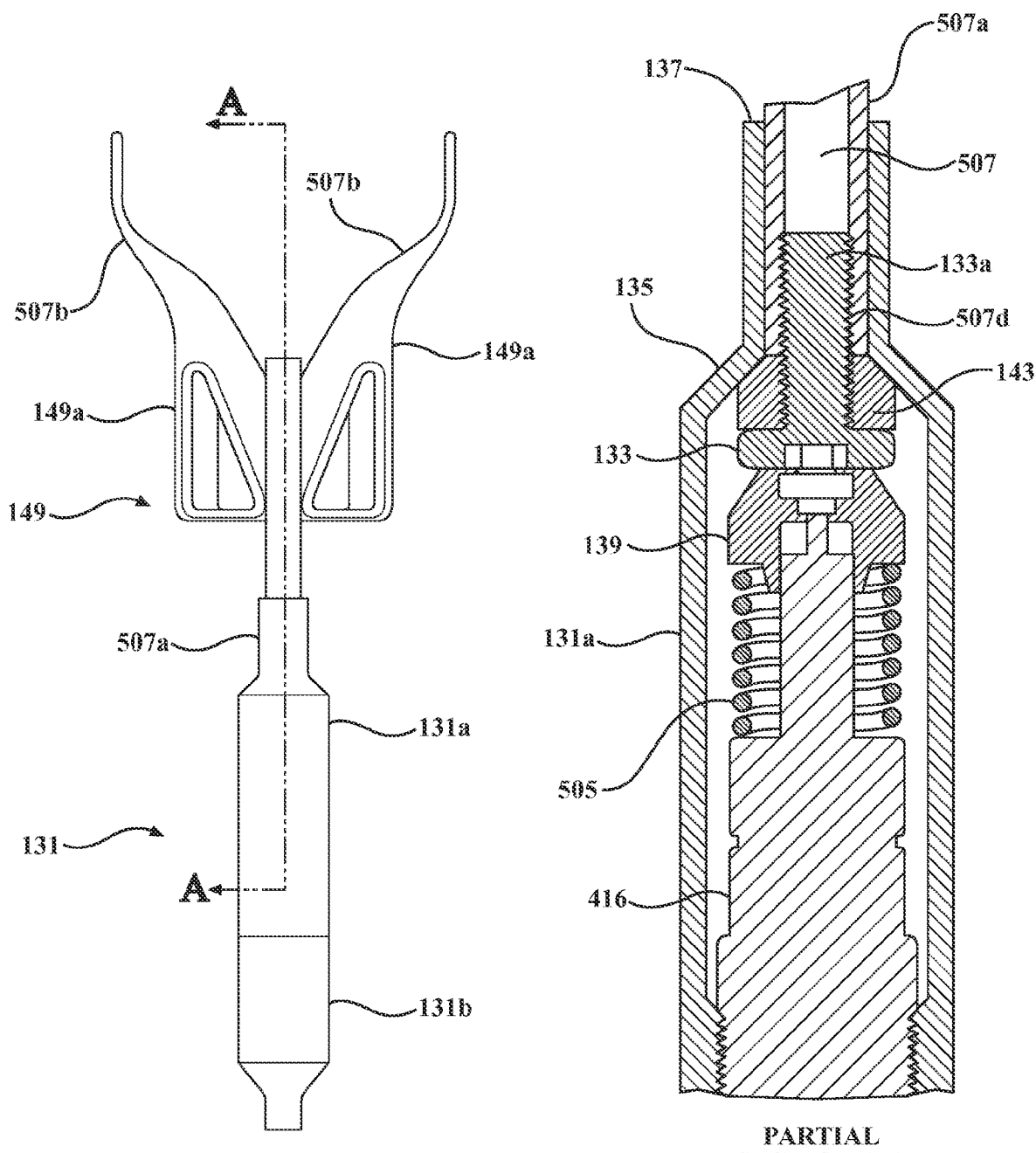
FIG. 49 is a perspective view of the shock absorber housing with the Y-shaped member inserted in the upper portion of the shock absorber housing.
FIG. 50 is partial sectional view of FIG. 49 taken along line A-A.
Figure 51:
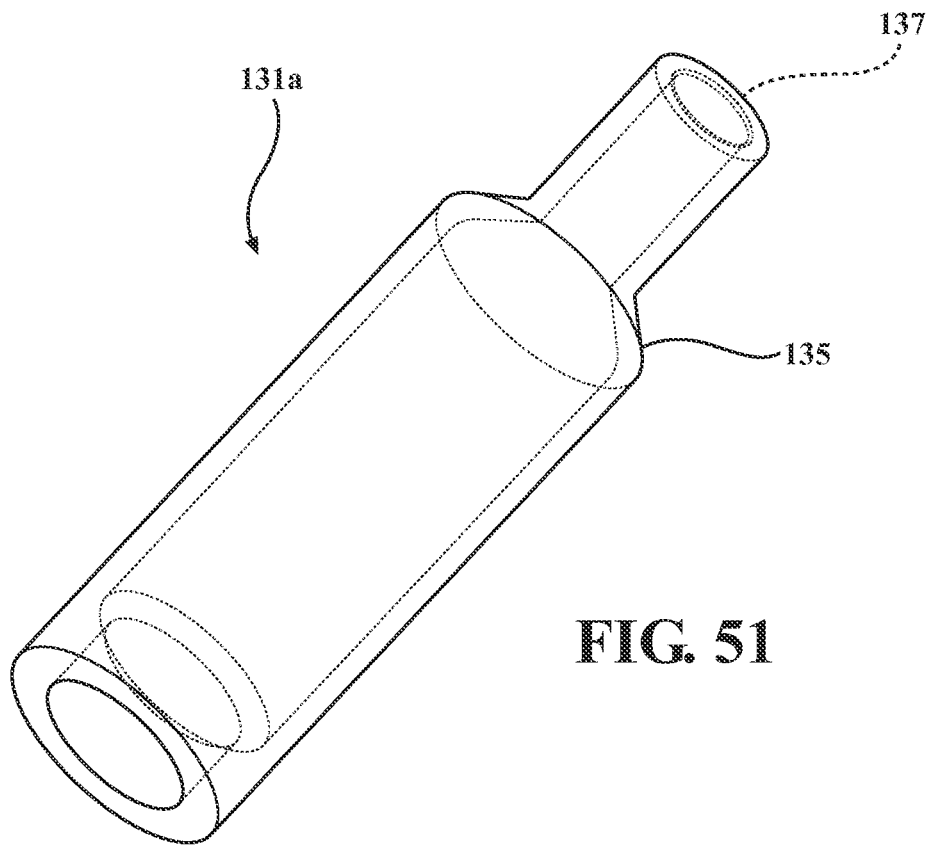
FIG. 51 is an isometric view of the upper portion of the shock absorber housing with an opening designed to accept the cylindrical end of the Y-shaped member and the threaded lower end 21 designed to accept the shock absorber.

With reference first to FIGS. 44, 49, 50 the lower strut assembly 414 includes a lower strut 426. The lower strut 426 is a generally elongated rigid member having a top end 426a. The shock absorber support assembly 498 includes a shock absorber housing 131 and a Y-shaped member 507. The shock absorber housing 131 includes a top portion 131a and a bottom portion 131b. The Y-shaped member 507 has a stem 507a, and a pair of prongs 507b. The pair of prongs 507b extend from the stem 507a and away from each other so as to provide space for a bent knee. A distal end of each the prong 507b is pivotably mounted to the upper sleeve assembly 412. A proximal end of the pair of prongs 507b include an attachment surface having a through hole 507c for supporting a fastening device 484, shown as a strap. The proximal ends of the pair of prongs 507b are fixedly attached to opposite sides of the stem 507a. The stem 507a includes a bottom end 507d is configured to engage the shock absorber 416. For example, the bottom end 507*d* of the stem 507*a* may include a bore 507*d* configured to receive the head of a screw 133 (shown in FIG. 59), the neck 133*a* of the screw 133 mounted within the bore 507*d*. The screw 133 is fixed to the top of the shock absorber 416 so as to drive the shock absorber. The top portion 131*a* of the shock absorber housing 131 includes a shoulder 135 having an opening 137 configured to fit the bottom end of the stem 507*a*. The shock absorber 416 is positioned between the stem 507*a* and the lower strut 426, wherein the shock absorber, stem 507*a* and lower strut 426 are coaxial with each other.

Figure 52:
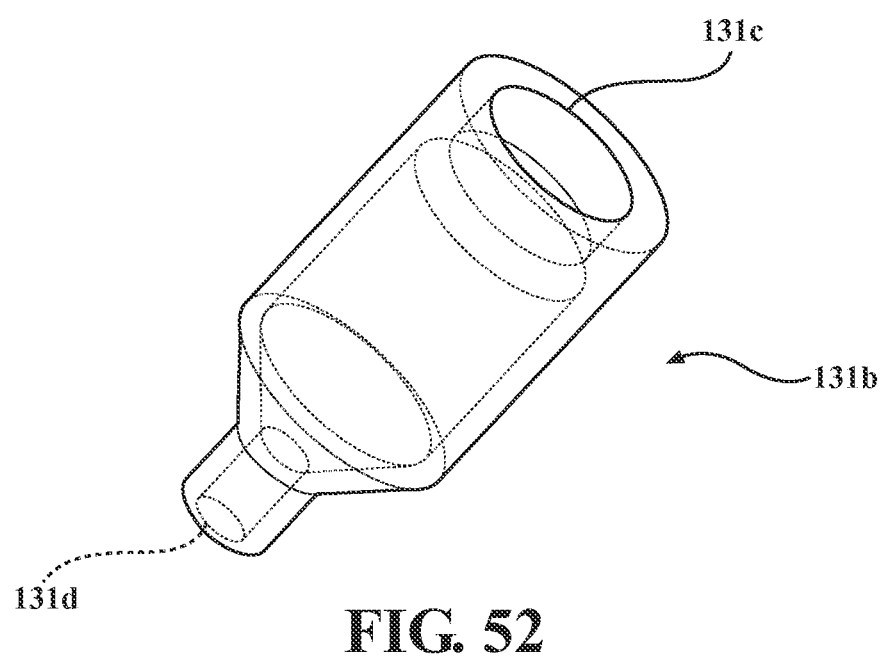
FIG. 52 is a perspective view of the lower end of the shock absorber housing.
Figure 60:
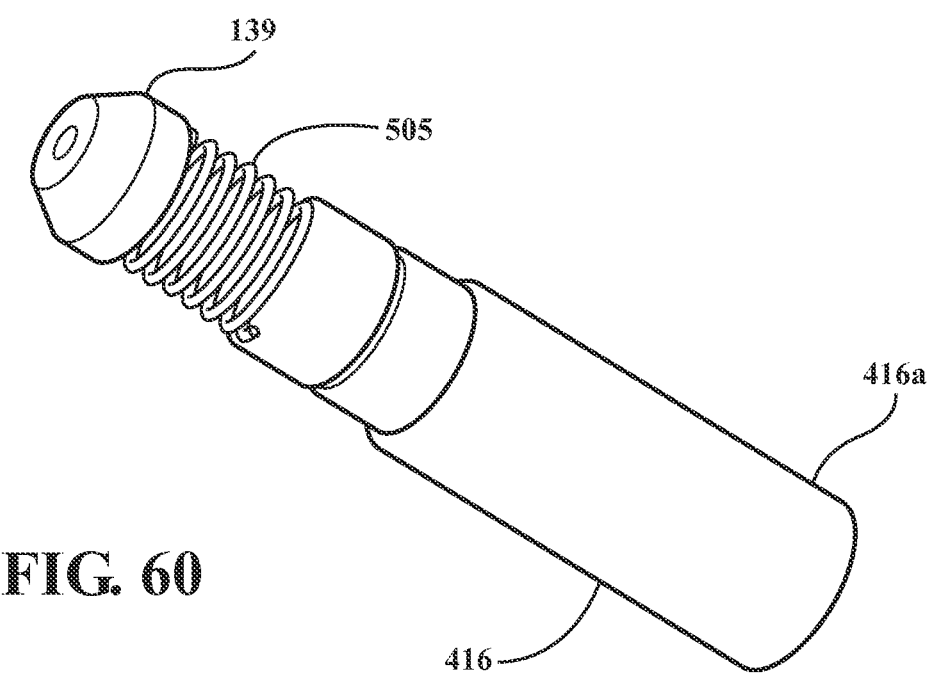
FIG. 60 is an isometric view of the shock absorber.

The shock absorber 416 represented in FIG. 60 is positioned inside of the shock absorber housing 131. The shock absorber 416 includes a threaded end 416*a*, and the bottom portion 131*b* of the shock absorber housing 131 includes a threaded bore dimensioned to threadedly engage the threaded end 416*a* of the shock absorber so as to provide an axial tolerance. The bottom portion 131*b* of the shock absorber housing 131 is depicted in FIG. 52 and the threads 131*c* may be threadedly engaged with a portion of the threaded end 416*a* of the shock absorber 416. The remaining portion of the threaded end 416*a* of the shock absorber 416 may be threadedly engaged with the threaded end 131*d* of top portion 131*a* so as to form the shock absorber housing 131 as shown in FIG. 49 and FIG. 50. The Shock absorber 416 also shows the biasing member 505 and a shock resistant load cap 139 in place.

The shock absorber support assembly 498 represented in FIG. 60 may be tuned for a load response configured to support the weight of its user. Further, the shock absorber housing 131 may be dimensioned to take into consideration packaging constraints. Accordingly, it should be appreciated that the exact dimensions provided herein are for illustrative purposes and are not limiting to the scope of the appended claims.

Figure 48:
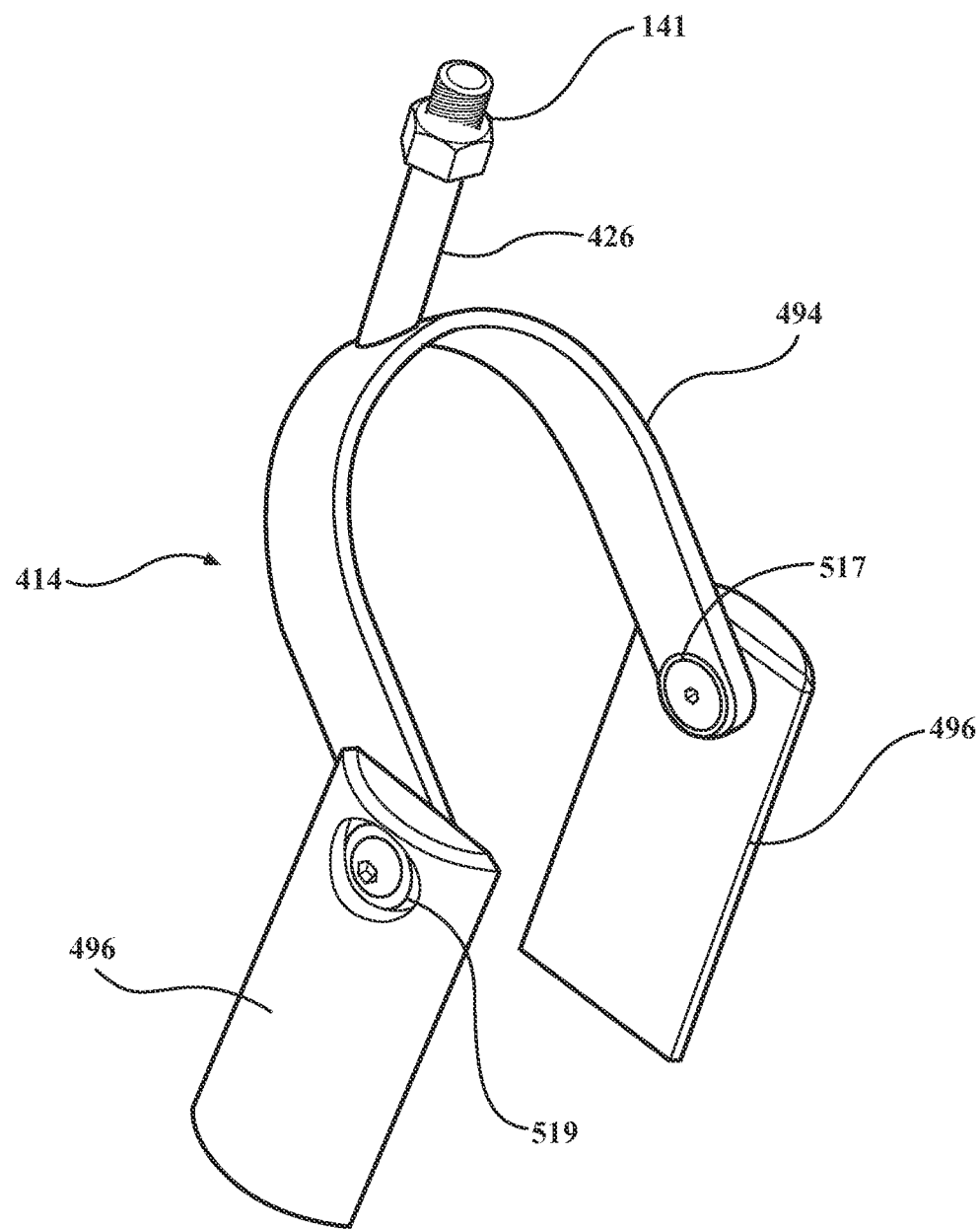
FIG. 48 is a perspective view of the lower strut assembly showing the retainer.

The bottom portion 131*b* of the shock absorber housing 131 is assembled to the lower strut 426, the lower strut 426 is fixedly mounted to a retainer 494 shown in FIG. 48. The bottom portion of the shock absorber housing 131 may be threadedly engaged to the lower strut 426 shock by use of internal threads 131*d* designed to correspond to the threads of the retainer 494 shown in FIG. 48. This threaded connection is designed to provide a fine height adjustment to accommodate individual user requirements. Lock nut 141 is to be firmly tightened to lock the assembly in the desired position.

The cylindrical end of the Y-shaped member 507 is designed to rotate freely and move up and down in the head unit 133 of the shock absorber housing 131. This unencumbered rotational movement ensures the freedom of angular movement of the foot of the user. The up and down movement is used to actuate the shock absorber.

The contact point between the Y-shaped member 507 and the shock absorber 416 is controlled by use of the head unit 133 and spacer 143 used to assemble the Y-shaped member 507 to the shock absorber 416 as shown in sectional view FIG. 50. Also the position of the shock absorber 416 in the shock absorber housing 131 can be controlled by varying the position of the shock absorber 416 with respect to the threaded ends of the top and bottom portions 131*a*, 131*b* of the shock absorber housing 131 shown in FIG. 51 and FIG. 52.

Depending upon the adjustments, at some point before the individual is fully standing, the Y-shaped member 507 starts making contact with the shock absorber support assembly 498 and the load transfer begins.

Figure 61:
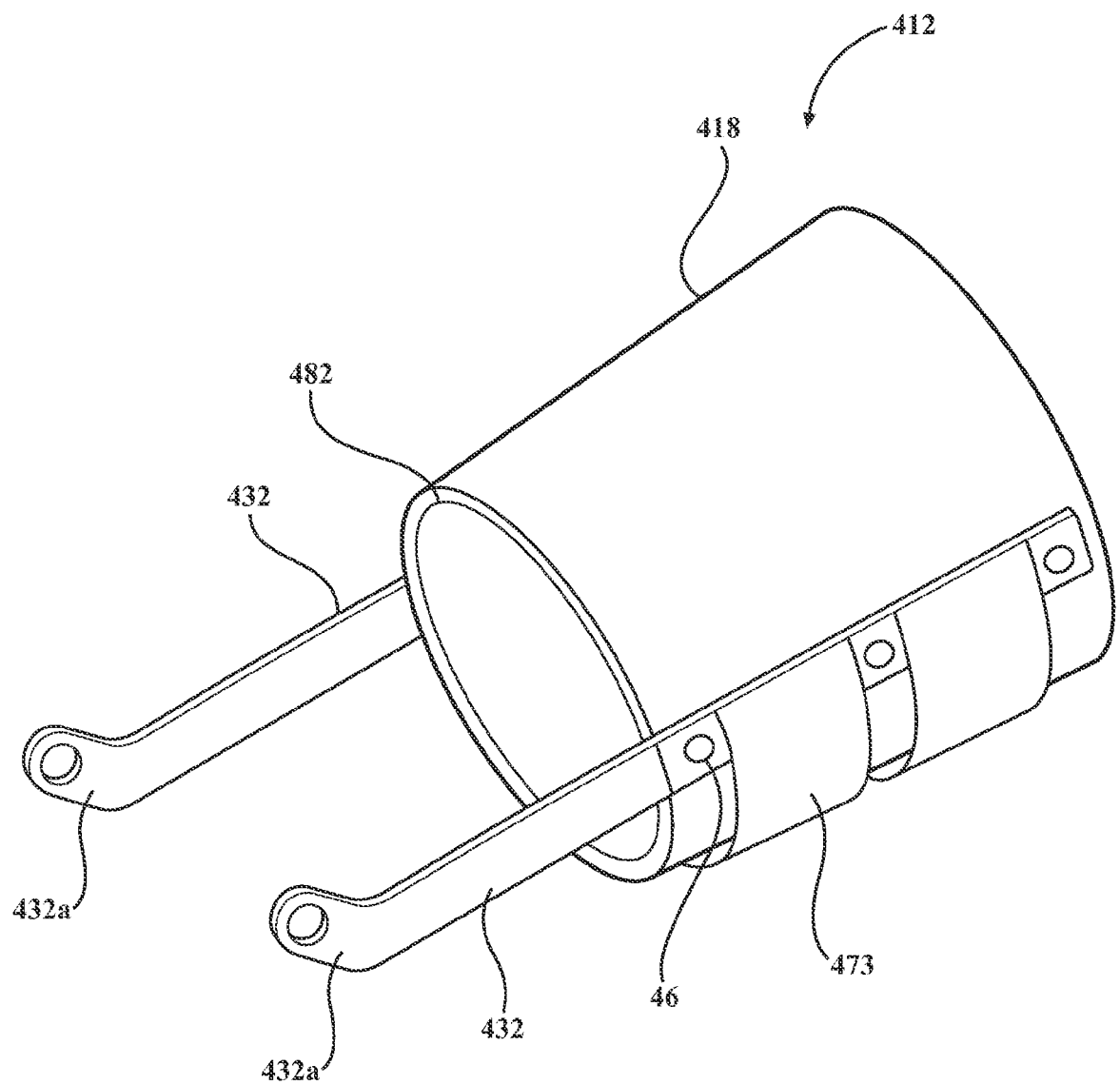
FIG. 61 is an isolated isometric view of the sleeve assembly with the upper struts in place as it would appear when fastened snugly with the straps to the thigh of the user.
Figure 62:
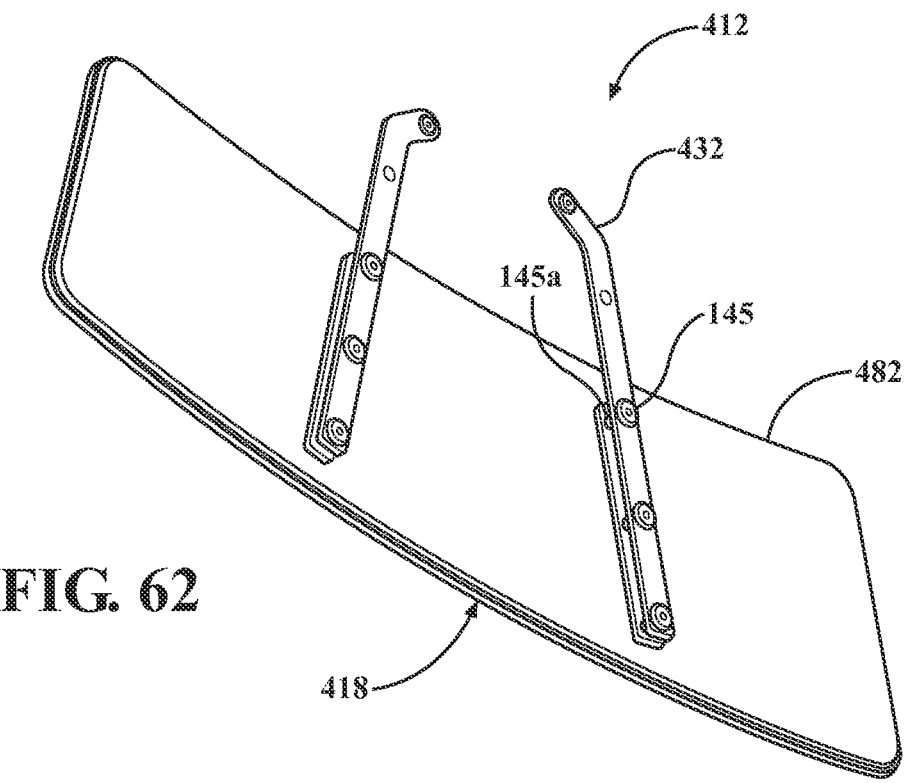
FIG. 62 is a perspective view of the sleeve assembly of FIG. 61 but as it would appear in the usual flat unrolled position.
Figure 63:
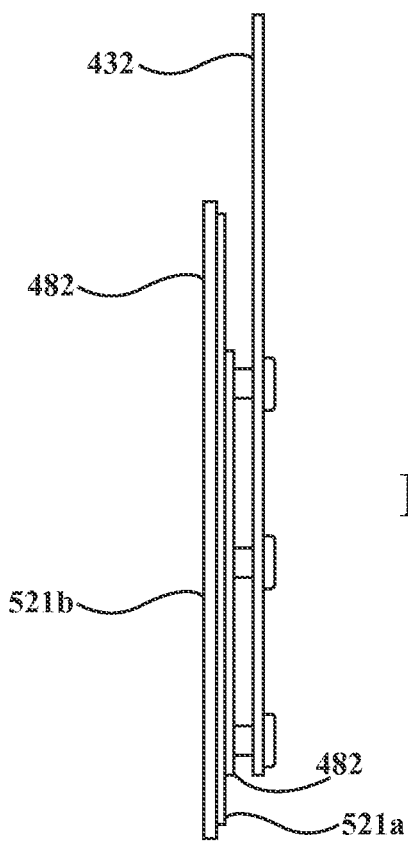
FIG. 63 is an end view of the sleeve assembly of FIG. 62.
Figure 64:
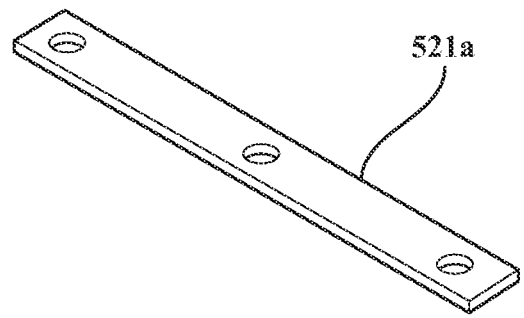
FIG. 64 is a perspective view of one of the spacers.
Figure 65:
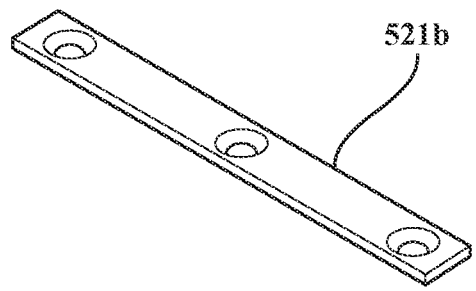
FIG. 65 is a perspective view of the other spacer.

FIG. 61 depicts the upper sleeve assembly 412. FIGS. 62 and 63 show the construction technique of one preferred design. The sleeve 418 is made out of a strong yet flexible material. A contact liner 482 is disposed on the surface that comes in contact with the skin and accordingly is made of non-allergenic strong and soft material designed for user comfort. The shape of the sleeve 418 is mainly dictated by load transfer capabilities and the positioning requirement of the upper struts 432 that have to be parallel to axis of the thigh and positioned symmetrically on opposite sides for optimum comfort and load transfer. The dimensions of the inner liner 482 are slightly larger than the dimensions of the sleeve 418 to which it is glued, thus the contact liner 482 protects the user from any harsh contacts with the edges of the sleeve 418. The upper struts 432 include an elongated body and a bottom end 432*a* which is angled relative to the elongated body. The bottom end 432*a* may be angled 45 degrees relative to the axis of the upper elongated body 432*b* of the upper strut. The bottom end 432*a* includes a hole 432*c* for pivotable connection to the prongs 507*b*.

Figure 57:
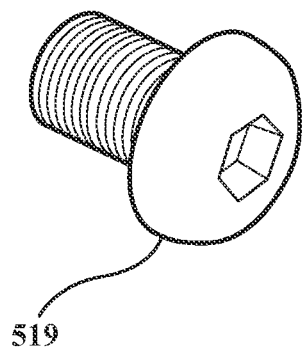
FIG. 57 is a perspective view of the screw.
Figure 58:
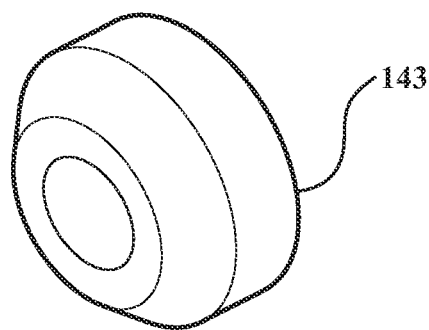
FIG. 58 is an isolated isometric view of the spacer for use in the shock absorber assembly.
Figure 59:
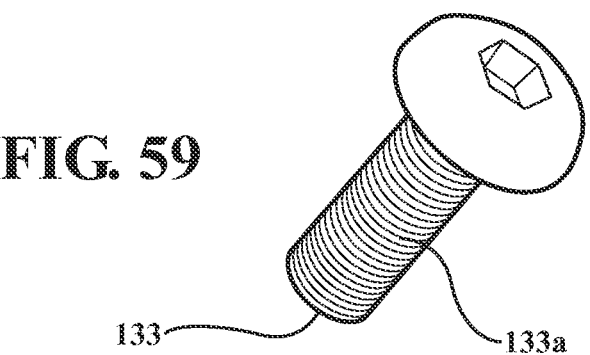
FIG. 59 is an isometric view of the threaded bolt with the flat head used to retain the Y-shaped member inside the shock absorber housing as shown in FIG. 50.
Figure 66:
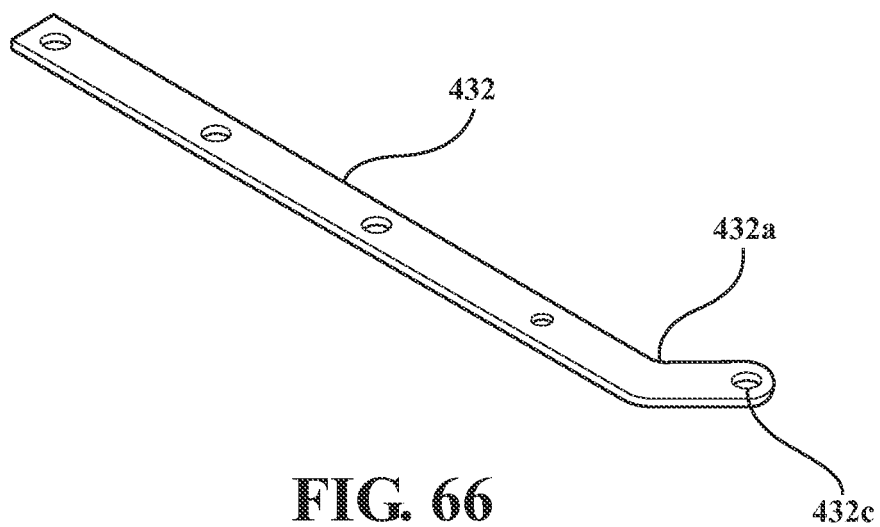
FIG. 66 is an isometric view of the upper strut.
Figures 67, 68:
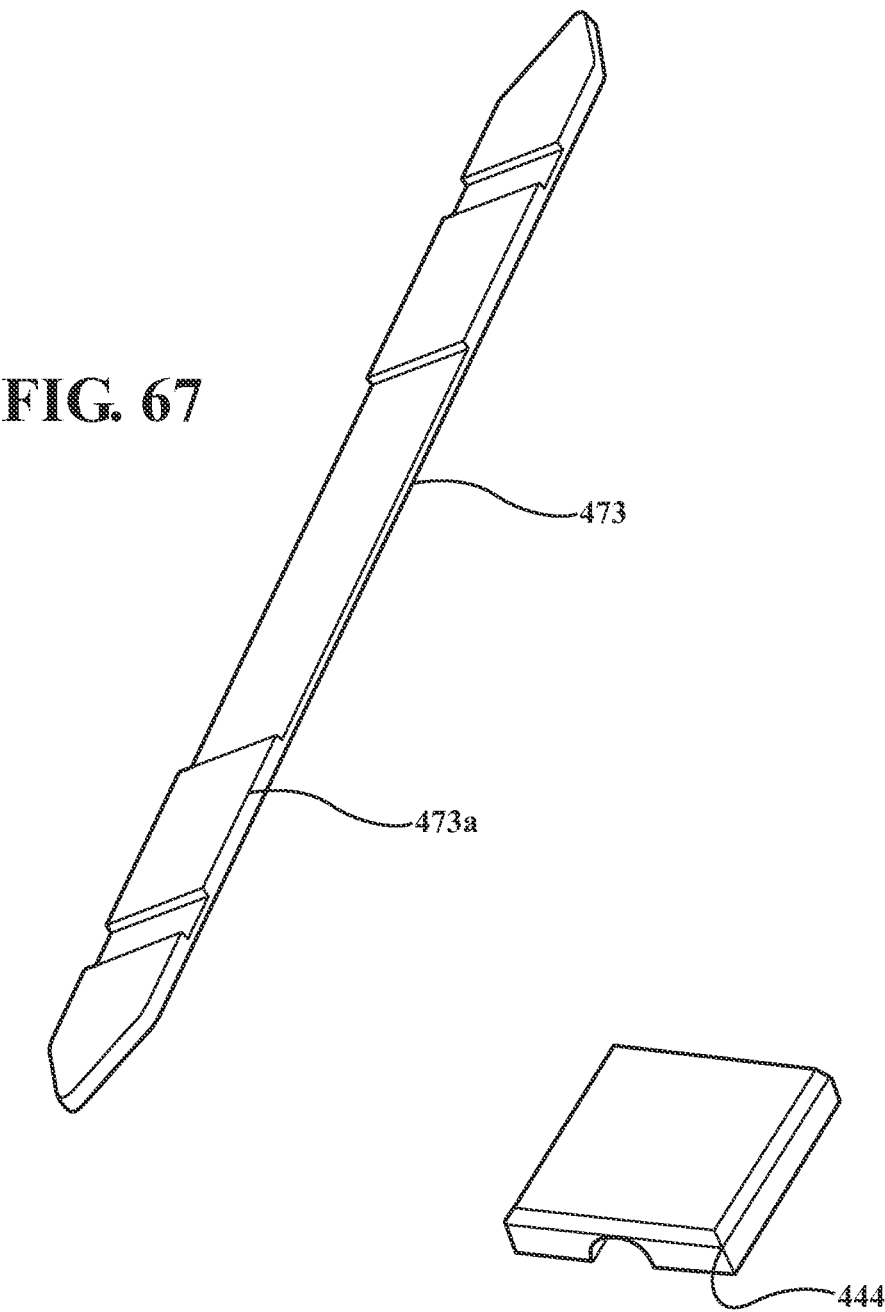
FIG. 67 is a perspective view of the fastening device for securing the sleeve.
FIG. 68 is a perspective view of a comfort pad.

FIG. 63 also depicts the construction technique used to attach the upper struts 432 also shown in detail in FIG. 66. Connector nut 517 shown in FIG. 56 and screws 519 shown in FIG. 57 are used to assemble the sleeve 418 and the upper struts 432 using the spacers 521*a* (see FIG. 64) and retaining bracket 521*b* (see FIG. 65) as shown in the end view presented in FIG. 63. It should be noted that the retainer retaining bracket 521*b* is not visible in this view as it is covered by the contact liner 482 to avoid harsh contact with the skin of the user. The fastening device 473 shown in FIG. 67 are anchored around the around the upper struts 432 when retaining the sleeve 418 around the thigh of the user. Nut 145 includes a pin head 145*a* which is also used to connect in a pivotal manner the Y-shaped member 507 to the upper struts 432 of the upper sleeve assembly 412 shown in FIG. 61.

Figure 46:
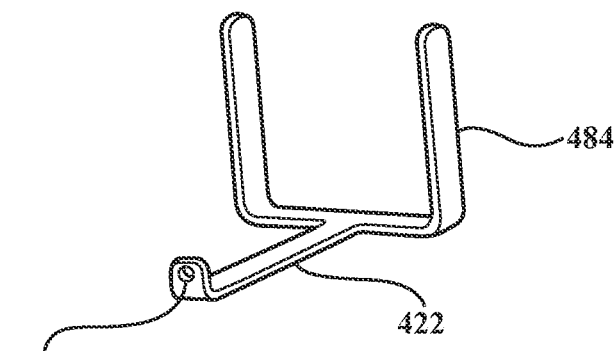
FIG. 46 is a perspective view of the shoe sole insert that is made an integral part of the shoe.
Figure 47:
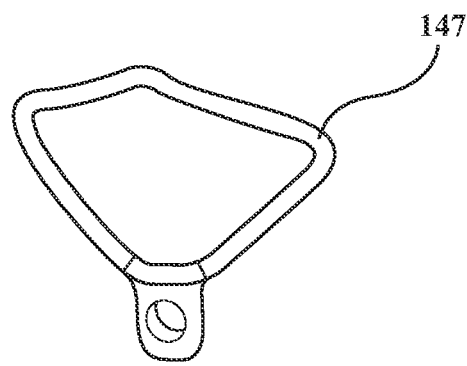
FIG. 47 is a perspective view of the anchor configured to attach to the shoe sole insert shown in FIG. 45.

Turning our attention to FIG. 46, the shoe sole insert 422 is provided. The shoe sole insert 422 is configured to support the knee brace 410 on the upwardly extending arms 484. The upwardly extending arms 484 can also provided with threaded holes for use with additional support straps in case those are desired for extra active applications. The shoe sole insert 422 may further include a small threaded hole 422*a* designed to retain fixedly the small anchor 147 shown in FIG. 46. The anchor 147 may be used in concert with the second lower attachment 430, shown as a strap in FIG. 54. The anchor 147 may provide further stability for extra vigorous activities. The second lower attachment 35 is to be wrapped snugly around the ankle of the user.

FIG. 48 is an embodiment of the lower strut assembly 414, showing the lower strut 426, retainer 494 and boots 496. The lower strut 426 is made integral to the retainer 494 by welding. The boots 496 include a bore 496*a* designed to closely fit over the upwardly extending arms 484 of the shoe sole insert 422 described above. The boots 496 are pivotally attached to the ends of the retainer 494 using the connecting nut 517 shown in FIG. 56 and retained with the a round head screw 519 shown in FIG. 57 which are mounted through hole 496*b*. The design of this subassembly supports the objective of providing freedom of movement along all axes. Specifically the boots 496 being free to slide up and down the upwardly extending arms 484 of the shoe sole inserts 422 provide vertical freedom of movement. The pivotally connected boots 496 by connector nuts 517 and screws 519 provide the angular movement freedom for the foot. The boot 496 is also configured to withstand the maximum load being transferred. Another feature of the boot 496 is the semicircular outer shape that helps minimize contact snags when an individual requires kneebooster devices on both his legs and the shoes on the right and left foot accidentally come in contact while in motion.

Figure 53:
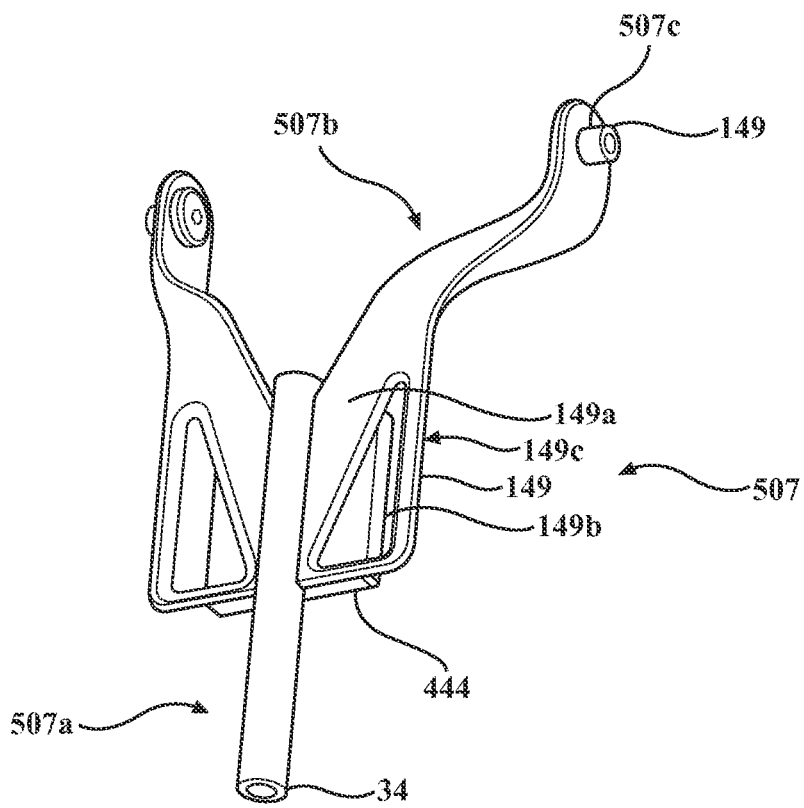
FIG. 53 is an isometric view of the Y-shaped member.

FIG. 53 depicts an isometric view of the Y-shaped member 507 that is to be pivotally connected through holes 507c using connector nuts 517 and screws 519 previously described to the upper sleeve assembly 412. The prongs 507b are integrally formed to the stem 507a by welding or other means.

Returning to FIG. 53 and the Y-shaped member 507 includes a first lower attachment support 149. The first lower attachment support 149 is dimensioned to support a first lower attachment 428, shown in FIG. 54 as a strap. The first lower attachment support 149 is shown as a pair of planar member 149a disposed on opposite sides of an upper portion of the stem 507a. Each of the planar members 149a includes an opening 149b dimensioned to receive the first lower attachment 428, the opening 149b defining a side edge 149c. Thus, the first lower attachment 428, shown as a strap in FIG. 54, may be mounted to the first lower attachment support 149, securing the calf and the Y-shaped member together by a fastener 428a, shown as Velcro in FIG. 54. A comfort pad 444 also shown in isolation in FIG. 68, may be mounted to the first lower attachment support 149. The comfort pad 444 may be centered along the axis of the stem 507a and retained fixedly in to the first lower attachment support 149 by use of suitable glue or other adequate means.

Figure 54:
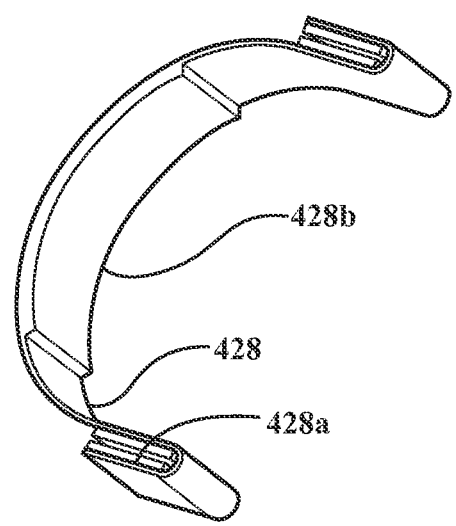
FIG. 54 is a perspective view of the first lower attachment.
Figure 55:
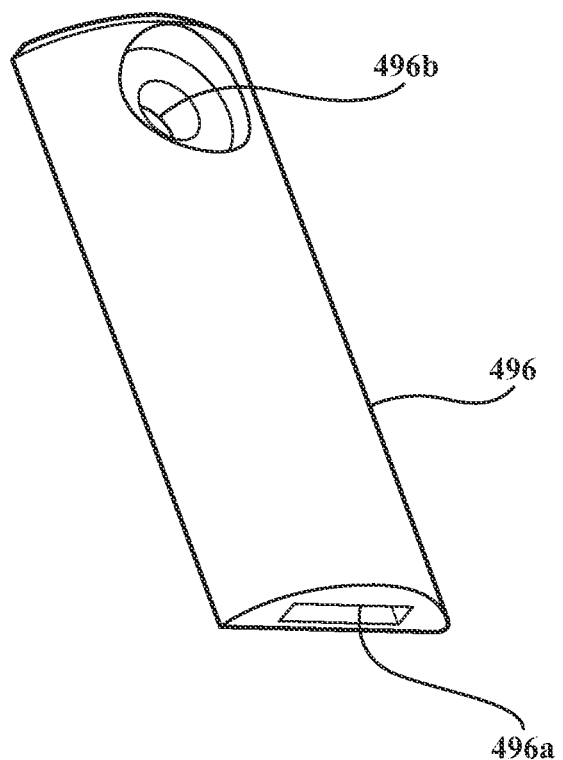
FIG. 55 is an isometric view of a boot 14.
Figure 56:
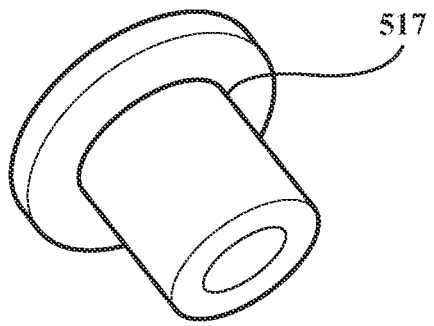
FIG. 56 is a perspective view the connecting nut.

FIG. 54 depicts an embodiment of the first lower attachment 428 as being a flexible strap provided with the comfort liner 428b and fastener 428a shown as Velco, however it should be appreciated that any other suitable fasteners 428a may be adaptable for use herein. The first lower attachment 428 is used for fastening the Y-shaped member 507 to the upper calf of the user. It should be appreciated that the brace 410 may include a second lower attachment 430, such as a like strap, may be configured to fasten the ankle of the user to the back end of the shoe 424 shown in FIG. 45 in conjunction with the retaining heel anchor 147 depicted in FIG. 47. The second lower attachment 430 may be needed for extreme user activities.

Figure 45:
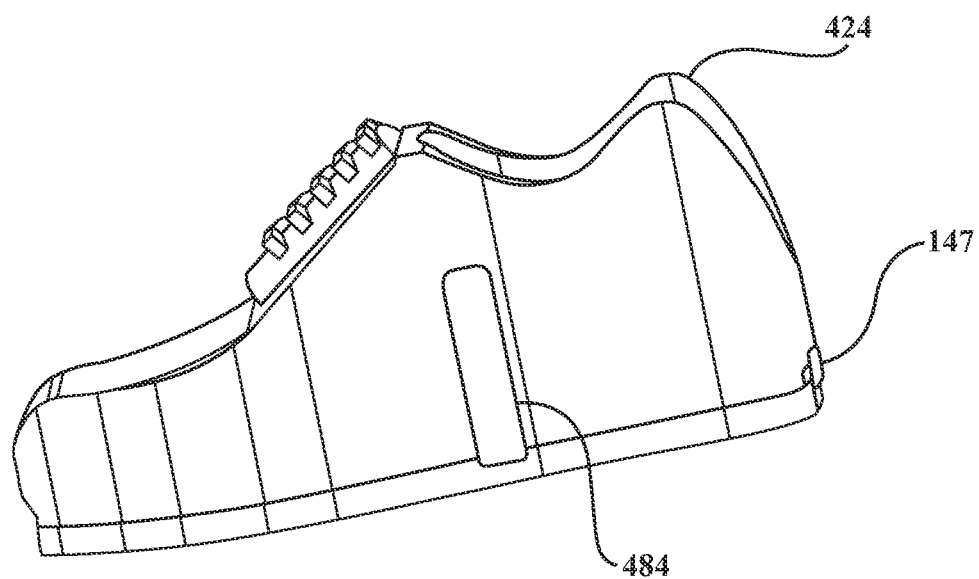
FIG. 45 is a perspective view of the shoe assembly with the metal insert and the optional ankle strap anchor in place.

In operation, the individual laces on the shoes 424 provided with the shoe sole insert 422 as shown in FIG. 45. The individual then places the upper sleeve assembly 412 on the thigh above the knee and engages the boots 496 shown in FIG. 48 onto the upwardly extending arms 484 of the shoe sole insert 422 as shown in FIG. 45 and FIG. 46. The blind end of the slot 17 in the boot 14 comes to rest on top of the vertical 6 in the shoe sole insert 422 shown in FIG. 46 on page 5/15.

At this point the strap 35 shown in FIG. 54 is used to strap snugly the Y-shaped assembly 30 through verticals 32 shown in FIG. 53 to the upper calf of the individual. This helps position the pivot point of the device with respect to the center of rotation of the knee of the user. The pivot point of the device is defined by the center of the holes 31 retaining the connecting nuts 13 fixedly attached to the Y-shaped member 507 30 by means of an interference fit as shown in FIG. 53. It should be appreciated that a strap of similar designed can also be used to fasten the shoe 424 around the ankle of the user using the heel anchor 147 shown in FIG. 47 as described previously.

The comfort pad 444 may be mounted to the stem 507a and configured to engage the tibia of the user. The first lower attachment 428 in conjunction with the fastener 428a may also support the comfort pad 444.

Subsequently the sleeve 418 is rolled around the thigh and wrapped snug tight with fastening device 473, shown as two straps 473 in FIG. 67. The two straps 473 include Velcro fasteners 473a also shown in the same FIG. 67. It is to be noted that as the user stands up the stem 507a of the Y-shaped member 507 slides down in to the shock absorber housing 131, through opening 137 as a result of the pivoting of the upper sleeve assembly 412, which is fixed to the thigh. When the leg is articulated, the knee brace 410 absorbs the shock imparted when the foot strikes the ground. In particular the pivot point of the knee brace 410 is positioned above the pivot point of the knee when the knee is bent, and when the leg is straightened out, the pivot point of the knee brace 410 is coaxial with that of the knee, causing the upper strut to engage the shock absorbers 16, and thus absorbing the load of a foot.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. An exoskeletal load bearing shock absorbing knee brace configured to be worn on a leg and designed to support a knee principally by reducing the load on the knee and absorbing peak shock loads when the leg is articulated, the brace coupled to both a thigh and a calf of a user; the knee brace comprising:
    an upper sleeve assembly having a sleeve configured to engage the thigh, and an upper strut;
    a lower strut assembly configured to engage the calf; and
    a pair of shock absorbers moveable between a compressed position and decompressed position, each of the pair of shock absorbers fixedly mounted to opposite sides of the lower strut assembly, each of the pair of shock absorbers having a drive shaft, wherein a distal end of the drive shaft is pivotably mounted to an upper sleeve about a first pivot point, the first pivot point being positioned above and forward of a pivot point of a bent knee so as to actuate the pair of shock absorbers to the decompressed position when the upper sleeve is pivoted relative to lower strut assembly by the articulation of the leg, wherein the drive shaft extends upwardly relative to the lower strut assembly when moving from the decompressed position to the compressed position so as to increase an axial length of the lower strut assembly, and wherein the drive shaft is configured to transmit a load to the thigh through the upper sleeve when moving from the decompressed position to the compressed position.

2. The knee brace as set forth in claim 1, further including a load bearing shoe sole insert configured to be positioned within a shoe of a user, the shoe sole insert pivotably mounted to a bottom end of the lower strut assembly.

3. The knee brace as set forth in claim 1, wherein the upper sleeve assembly includes a sleeve, the sleeve having a conical shape, having an upper opening and a lower opening, the upper opening having a diameter larger than the diameter of the lower opening so as to accommodate the shape of the thigh.

4. The knee brace as set forth in claim 1, wherein the shock absorbers include a biasing member configured to urge the shock absorber piston to the decompressed position, the pair of shock absorbers pivotably mounted to the upper sleeve assembly, the biasing member further configured to urge the upper sleeve assembly upwardly so as to help bias the upper sleeve assembly against the upper thigh.

5. The knee brace as set forth in claim 1, wherein the upper sleeve assembly includes a strap configured to fix the upper sleeve in place with respect to the thigh, wherein the pair of shock absorbers absorb substantially all of the load from an articulated leg.

6. The knee brace as set forth in claim 2, wherein the lower strut assembly includes a lower strut, the lower strut disposed along an axis, a bottom end of the lower strut is mounted to a heel portion of the shoe sole insert.

7. The knee brace as set forth in claim 6, further including a retainer configured to hold each of the pair of shock absorbers and a calf support having a semicircular face configured to seat the calf, the attachment mounted to a top end of the lower strut opposite the bottom end, each of the pair of shock absorbers are fixedly mounted to an outer edge of a respective attachment so as to position each of the pair of shock absorbers on a respective outer side of and above the knee.

8. The knee brace as set forth in claim 6, wherein the lower strut assembly includes a boot disposed on a bottom end of the lower strut, the boot having a bore, and wherein the shoe sole insert includes a pin head disposed on a back end of the shoe sole insert, pin head pivotably mounted to shoe sole insert, the bore dimensioned to slidingly receive the pin head so as to allow the shoe sole insert to pivot relative to the lower strut.

9. The knee brace as set forth in claim 8, wherein the lower strut assembly includes a first lower attachment, the first lower attachment configured to engage the calf so as to secure the lower strut assembly to the calf.

10. The knee brace as set forth in claim 9, wherein the first lower attachment is a strap.

11. The knee brace as set forth in claim 10, wherein the strap is formed from a flexible material and includes a fastening device configured to retain the strap to itself.

12. The knee brace as set forth in claim 8, wherein the lower strut assembly includes a second lower attachment, the second lower attachment disposed on the bottom end of the lower strut assembly and configured to engage a foot, so as to secure the shoe sole insert to the foot.

13. The knee brace as set forth in claim 12, wherein the first lower attachment is a strap.

14. The knee brace as set forth in claim 13, wherein the strap is formed from a flexible material and includes a fastening knee brace configured to retain the strap to itself.

15. The knee brace as set forth in claim 8, wherein the shoe sole insert includes a pair of upwardly extending arms rigidly fixed to the shoe sole insert, each of the pair of upwardly extending arms pivotally connected to the lower strut, the shoe sole insert having a base dimensioned to support the foot of a user.

16. The knee brace as set forth in claim 1, wherein the lower strut assembly includes a pair of lower struts, each of the pair of lower struts are generally axial, and each of the pair of lower struts is mounted to a respective one of the pair of shock absorbers, the pair of lower struts are spaced apart from each other so as to be disposed on opposite sides of the calf.

17. The knee brace as set forth in claim 16, further including a load bearing shoe sole insert configured to be positioned within a shoe of a user, the shoe sole insert including a base dimensioned to support the foot of the user, a pair of upwardly extending arms rigidly fixed to the shoe sole insert, the pair of upwardly extending arms pivotably connected to the pair of lower struts.

18. The knee brace as set forth in claim 1, further including a load bearing shoe sole insert configured to be positioned within a shoe of a user, the shoe sole insert including a base dimensioned to support the foot of the user, a pair of upwardly extending arms rigidly fixed to the shoe sole insert, the lower strut assembly further includes a retaining sleeves, a lower strut having a top end opposite a bottom end, and a retainer, the retaining sleeves disposed on the top end of the lower strut and configured to hold each of the pair of shock absorbers, the retainer disposed on the bottom end of the lower strut the ends of the retainer are pivotably mounted to a respective pair of upwardly extending arms so as to position the lower strut in front of the calf of the user.

19. The knee brace as set forth in claim 1, wherein the lower strut assembly further includes a shock absorber support assembly, the shock absorber support assembly having a tube, a bracket, a biasing member, and a Y shaped member, the lower strut assembly further including a lower strut, the lower strut being a generally elongated and rigid member having a top end, wherein the tube is dimensioned to cover a bottom portion of the lower strut wherein a top end of the lower strut is exposed, the biasing member disposed on a top end of the tube, the bracket is fixedly mounted to the tube and is configured to hold the pair of shock absorbers so as to position the shock absorbers in front of a tibia, the Y shaped member having a stem and a pair of prongs extending from the stem and away from each other so as to provide space for a bent knee, the ends of the prongs are pivotably mounted to the upper strut assembly and the stem having a bore dimensioned to engage the top end of the lower strut wherein the shock absorbers and biasing members are operative to urge the stem upwards relative to the bottom end of the lower strut.

20. The knee brace assembly as set forth in claim 19, wherein the bottom ends of each of the pair of upper struts are angled forward with respect to the thigh, a forward portion of the bottom ends are pivotably attached to the end of a respective prong.

21. The knee brace assembly as set forth in claim 19, wherein the bottom ends of each of the pair of upper struts is angled generally 45 degrees from the axis of the pair of upper struts.

22. The knee brace as set forth in claim 19, wherein the shock absorber support further includes a calf support and a first lower attachment mounted to the calf support, the first lower attachment configured to engage the calf so as to secure the lower strut assembly to the calf.

23. The knee brace as set forth in claim 22, wherein the first lower attachment is a strap.

24. The knee brace as set forth in claim 19, further including a load bearing shoe sole insert configured to be positioned within a shoe of a user, the load bearing shoe sole insert including a base configured to support the foot and pivotably attached to the bottom end of the lower strut.

25. The knee brace as set forth in claim 24, wherein the lower strut assembly further includes a retainer disposed on a bottom end of the lower strut, and the load bearing shoe sole includes a pair of upwardly extending arms disposed on opposite sides of the base, the pair of upwardly extending arms are rigid and generally orthogonal to the base, the ends of the retainer are pivotably mounted to a respective pair of upwardly extending arms so as to position the lower strut in front of the calf of the user.

26. The knee brace as set forth in claim 25, wherein the retainer is an arched member and further including a pair of boots pivotably mounted to opposing side ends of the retainer, each of the boots detachably engaged with a respective one of the pair of upwardly extending arms.

27. The knee brace as set forth in claim 19, wherein the prongs of the Y shaped member are twist about an axis of the respective prong.

28. The knee brace as set forth in claim 1, wherein the lower strut assembly includes a lower strut and a shock absorber support assembly includes a shock absorber support assembly, the shock absorber support assembly having a shock absorber housing, and a Y shaped member, the lower strut assembly further including a lower strut, the lower strut being a generally elongated and rigid member having a top end, the shock absorber housing having a top portion and a bottom portion, the Y shaped member having a stem, and a pair of prongs, the pair of prongs extending from the stem and away from each other so as to provide space for a bent knee, a distal end of the prongs are pivotably mounted to the upper strut assembly, a proximal end of the pair of prongs include an attachment surface having a through hole for supporting a strap, the proximal ends of the pair of prongs are fixedly attached to opposite sides of the stem, the stem having a bottom portion having an opening configured to receive the lower strut, the top portion of the shock absorber housing having an opening configured to fit the bottom portion of the stem, the tubing dimensioned to house the shock absorber, wherein articulation of the leg engages the stem downwardly, the impact being absorbed by the shock absorber.

29. The knee brace as set forth in claim 28, wherein the bottom ends of each of the pair of upper struts are angled forward with respect to the thigh, a forward portion of the bottom ends are pivotably attached to the end of a respective prong.

30. The knee brace as set forth in claim 28, further including a load bearing shoe sole insert configured to be positioned within a shoe of a user, the load bearing shoe sole insert including a base configured to support the foot, the load bearing shoe sole insert pivotably attached to the bottom end of the lower strut.

31. The knee brace as set forth in claim 30, wherein the lower strut assembly further includes a retainer disposed on a bottom end of the lower strut, and the load bearing shoe sole includes a pair of upwardly extending arms disposed on opposite sides of the base, the pair of upwardly extending arms are rigid and generally orthogonal to the base, the ends of the retainer are pivotably mounted to a respective pair of upwardly extending arms so as to position the lower strut in front of the calf of the user.

32. The knee brace as set forth in claim 31, further including a pair of boots pivotably mounted to opposing side ends of the retainer, the boots including a slot configured to receive a respective upwardly extending arm.

33. The knee brace assembly as set forth in claim 28, wherein the lower strut assembly further includes a pad mounted to the stem and configured to engage the tibia of the user.

34. The knee brace as set forth in claim 27, wherein the shock absorber and the lower strut and the stem are coaxial with each other.

35. The knee brace as set forth in claim 29, wherein the shock absorber includes a threaded end, and wherein the bottom portion of the shock absorber housing includes a threaded bore dimensioned to threadedly engage the threaded end of the shock absorber so as to provide an axial tolerance.

* * * * *